(12) United States Patent
Noel et al.

(10) Patent No.: US 6,406,648 B1
(45) Date of Patent: Jun. 18, 2002

(54) METHOD OF MAKING SHAPED FOAM IMPLEMENTS

(75) Inventors: John Richard Noel; John Collins Dyer; Thomas Allen DesMarais, all of Cincinnati; Paul Martin Lipic, West Chester; John Lee Hammons, Hamilton, all of OH (US)

(73) Assignee: The Procter & Gamble Company, Cincinnati, OH (US)

( * ) Notice: Subject to any disclaimer, the term of this patent is extended or adjusted under 35 U.S.C. 154(b) by 29 days.

(21) Appl. No.: 09/698,921

(22) Filed: Oct. 27, 2000

Related U.S. Application Data
(60) Provisional application No. 60/163,213, filed on Nov. 2, 1999.

(51) Int. Cl.[7] .................................................. C08J 9/28
(52) U.S. Cl. .................... 264/46.4; 264/41; 264/297.1; 521/64
(58) Field of Search ...................... 264/41, 46.4, 297.1; 521/64

(56) References Cited

U.S. PATENT DOCUMENTS

| | | | |
|---|---|---|---|
| 2,747,575 A | 5/1956 | Mercer ........................ 128/290 |
| 3,256,219 A | 6/1966 | Will ............................ 260/2.5 |
| 3,903,232 A | 9/1975 | Wood et al. ................. 264/157 |
| 4,049,592 A | 9/1977 | Marans et al. ............... 260/2.5 |
| 4,110,276 A | 8/1978 | Desmarais .................. 521/123 |
| 4,425,130 A | 1/1984 | Desmarais .................. 604/389 |
| 4,613,543 A | 9/1986 | Dabi ........................... 428/304.4 |
| 4,752,349 A | 6/1988 | Gebel ......................... 156/267 |
| 4,804,380 A | 2/1989 | Lassen et al. .............. 604/385.1 |
| 4,839,395 A | * 6/1989 | Masamizu et al. ............ 521/64 |
| 4,950,264 A | 8/1990 | Osborn, III ............... 604/385.1 |
| 5,009,653 A | 4/1991 | Osborn, III ............... 604/385.1 |
| 5,147,345 A | 9/1992 | Young et al. ................ 604/378 |
| 5,149,720 A | * 9/1992 | DesMarais et al. ............ 521/64 |
| 5,189,070 A | * 2/1993 | Brownscombe et al. ....... 521/64 |
| 5,260,345 A | 11/1993 | Desmarais et al. .......... 521/148 |
| 5,268,224 A | 12/1993 | Desmarais et al. .......... 428/286 |
| 5,292,777 A | * 3/1994 | DesMarais et al. ............ 521/64 |
| 5,318,554 A | 6/1994 | Young et al. ................ 604/378 |
| 5,352,711 A | * 10/1994 | DesMarais .................... 521/64 |
| 5,387,207 A | 2/1995 | Dyer et al. .................. 604/369 |
| 5,670,101 A | * 9/1997 | Nathoo et al. .............. 264/45.8 |
| 5,817,271 A | * 10/1998 | Congleton et al. ........... 264/400 |
| 5,849,805 A | 12/1998 | Dyer ............................ 521/64 |
| 5,873,869 A | 2/1999 | Hammons et al. ........ 604/385.1 |
| 5,899,893 A | 5/1999 | Dyer et al. .................. 604/358 |
| 6,204,298 B1 | * 3/2001 | DesMarais et al. ............ 521/64 |
| 6,261,679 B1 | * 7/2001 | Chen et al. ............... 428/317.9 |
| 6,299,808 B1 | * 10/2001 | Mork et al. ................. 264/46.4 |

FOREIGN PATENT DOCUMENTS

| | | |
|---|---|---|
| WO | WO 94/16658 | 8/1994 |
| WO | WO 99/01095 | 1/1999 |

\* cited by examiner

*Primary Examiner*—Allan R. Kuhns
(74) *Attorney, Agent, or Firm*—Edward J. Milbrada; Ken K. Patel; Steven W. Miller

(57) ABSTRACT

Described is a method of forming and curing high internal phase emulsions (HIPEs) into shaped three dimensional foam implements. In general the method uses the steps of: providing a HIPE, depositing the HIPE into a mold cavity having a predetermined three dimensional shape, curing the HIPE in the mold cavity to form a HIPE foam, and stripping the HIPE foam from the mold cavity to form the three dimensional foam implement. The molded implements are widely useful as components in absorbent articles, toys, insulation, and other uses where a combination of low density and tridimensional shape are desired.

19 Claims, 6 Drawing Sheets

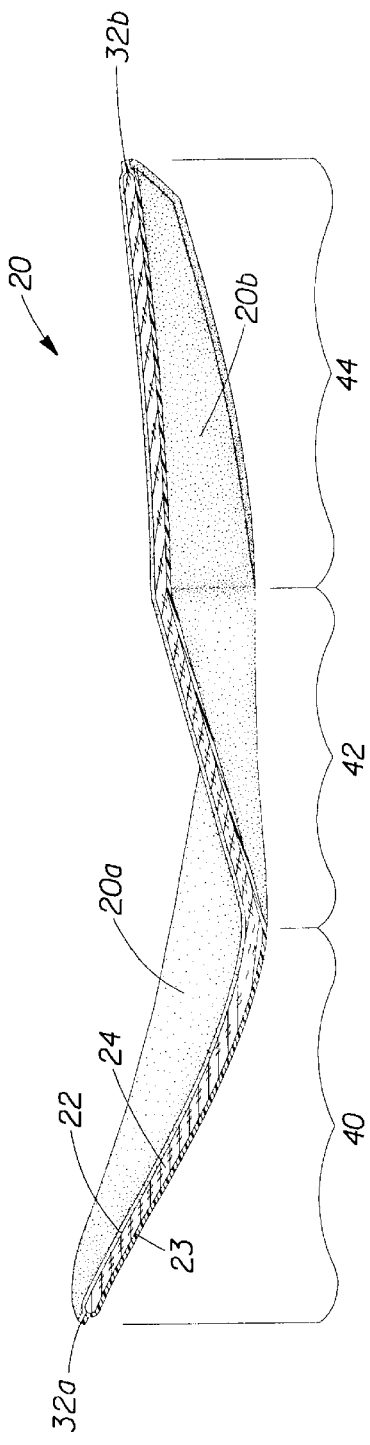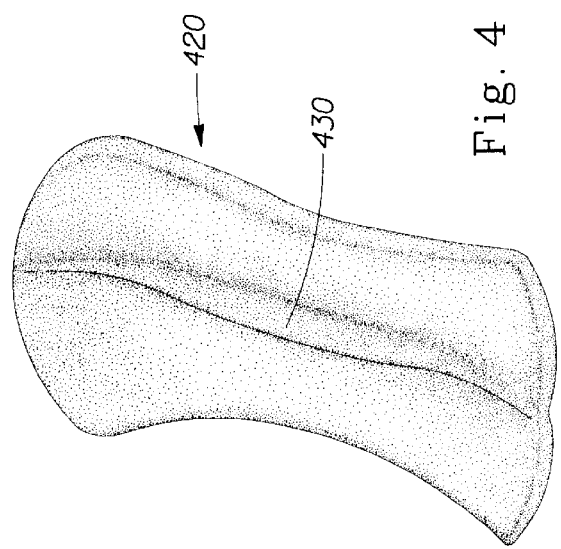
Fig. 2
Fig. 3
Fig. 4

METHOD OF MAKING SHAPED FOAM IMPLEMENTS

This application claims the benefit of provisional application No. 60/163,213, filed Nov. 2, 1999.

FIELD OF THE INVENTION

The present invention relates to tridimensional shaped foam implements and methods of making such implements. More particularly, the present invention relates to tridimensional absorbent components useful in absorbent articles such as sanitary napkins, panty liners, tampons, and the like and methods of making such shaped absorbent components.

BACKGROUND OF THE INVENTION

Absorbent articles such as sanitary napkins, pantiliners, and incontinence pads are devices that are typically worn in the crotch region of an undergarment. These devices are designed to absorb and retain liquid and other discharges from the human body and to prevent body and clothing soiling. Sanitary napkins are a type of absorbent article worn by women in a pair of panties that is normally positioned between the wearer's legs, adjacent to the perineum. Sanitary napkins of a wide variety of shapes and dimensions are currently used by women for the collection of menses and other bodily discharges.

In the past, a number of efforts have been directed at providing sanitary napkins that maintain contact with the wearer's body. One attempt to provide such body contact is disclosed in U.S. Pat. No. 2,747,575 issued May 29, 1956 to Mercer. The Mercer patent discloses a catamenial bandage having a longitudinal hump which bulges towards and may contact the body of the wearer. The catamenial bandage described in the Mercer patent suffers from several disadvantages, however. For instance, the size and shape of the absorbent pad and hump in the Mercer bandage appear to limit the conditions under which the bandage is able to maintain contact with (and conform to) the body of the wearer. The portions of the bandage that lie laterally to the sides of the hump are not thin and flexible. In addition, the hump of the Mercer bandage is made of a cellulosic material, and, as a result, may tend to collapse and become permanently distorted during use.

U.S. Pat. No. 4,425,130 issued to DesMarais on Jan. 10, 1984, discloses a compound sanitary napkin that comprises a primary menstrual pad and a panty protector joined to one another at their corresponding ends in such a manner that the two constituents are free to move relative to one another along essentially their entire common length. The primary menstrual pad is intended to absorb the bulk of the bodily fluids discharged by the user, while the panty protector is intended to protect the user's garments from soiling. In use, the relative freedom of movement between the primary menstrual pad and the panty protector serves to maintain the primary menstrual pad adjacent the user's crotch region while the panty protector remains associated with the user's undergarment.

The current tendency has been to develop sanitary napkins that are increasingly thinner, and thus more comfortable and less obtrusive than prior sanitary napkins. Recently, efforts have been directed at developing thin sanitary napkins which have the capacity to absorb and contain medium to high menstrual discharges. Previously, such discharges could only be handled by relatively thick sanitary napkins. Examples of thin sanitary napkins having capacities great enough to handle medium to high menstrual flows are disclosed in U.S. Pat. Nos. 4,950,264 and 5,009,653, issued to Osborn, III, on Aug. 21, 1990 and Apr. 23, 1991, respectively.

It is also desirable that sanitary napkins, not only maintain contact with, but conform as closely as possible to the wearer's body. Such a body-conforming capability increases the effectiveness of the sanitary napkin by reducing the possibility that menses will travel beyond the perimeter of the sanitary napkin and leak. There have been a number of recent efforts to provide sanitary napkins and other absorbent articles with improved body-conforming characteristics. In addition to serving as examples of thin sanitary napkins, the sanitary napkins disclosed in the above-mentioned Osborn patents also serve as examples of anatomically-conforming sanitary napkins. While the sanitary napkins disclosed in the Osborn patents work quite well, the search for improved sanitary napkins has continued.

For example, published PCT Application Serial No. WO 94/16658, published on Aug. 4, 1994, discloses a generally thin, flexible sanitary napkin which has a central absorbent hump, and is capable of handling medium to high menstrual flows. The hump is particularly useful in fitting into the space between the wearer's labia to more readily intercept menses and other bodily discharges when they leave the wearer's body. The search, however, has continued for Improved sanitary napkins, particularly sanitary napkins that will achieve even better fit within the space between the wearer's labia majora, and which are more adept at absorbing blood-based liquids, such as menses.

Three dimensional absorbent articles designed for absorbing blood-based liquids are also known. Typically such articles are intended to enable intralabial interception of such fluids with extralabial storage of the absorbed fluids. One attempt to increase the body fitting capability of sanitary napkin has been to combine both a cupped and a humped shape in the same article, typically achieving a sanitary napkin having a flattened front portion combined with a raised rear portion, in order to better fit the variations in the anatomy in longitudinal direction. One such structure is described in U.S. Pat. No. 4,804,380, issued to Lassen, et al. on Feb. 14, 1989 which describes an article that has a substantially flat or concave front portion intended to cover area of the mons pubis, and a longitudinally oriented raised peak in the rear portion that is said to adjust and mold into the inverted-V shape of the rear portion of the labia. Although this type of structure does provide a sanitary napkin with a certain degree of three dimensionality, such structures still cannot actually fit the various complex body shapes of the female anatomy that comprise nonlinear grooves and nonplanar surfaces. The sanitary napkin of the '380 reference is provided with its three dimensionality by mechanically shaping an initially flat structure. This means, for example, that the raised peak in the rear portion thereof has a rectilinear profile when seen in side view, and therefore it fails to conform properly to the corresponding non-linear profile of a wearer's anatomy as seen in a longitudinal direction.

Another example of an absorbent article having three dimensionality is described in published PCT application Ser. No. WO 99/01095 ('095 application), published in the name of the Procter & Gamble Company on Jan. 14, 1999. The devices described therein have a profile along the longitudinal centerline that provides improved conformity to human female anatomical features allowing improved bodily fit. However, improvements are still needed because the complex set of fold lines and planar surfaces is difficult to fabricate. Further, the contours of the device are substantially linear and planar compared to the nonlinear nature of anatomical surfaces (See, for example, FIG. 4 thereof).

The development of highly absorbent articles for blood and blood-based liquids such as catamenial pads (e.g., sanitary napkins), tampons, wound dressings, bandages and surgical drapes can be challenging. Compared to water and urine, blood and blood based liquids such as menses are relatively complex mixtures of dissolved and undissolved components (e.g., erythrocytes or red blood cells). In particular, blood-based liquids such as menses are much more viscous than water and urine. This higher viscosity hampers the ability of conventional absorbent materials to efficiently and rapidly transport these blood-based liquids to regions remote from the point of initial discharge. Undissolved elements in these blood-based liquids can also potentially clog the capillaries of these absorbent materials. This makes the design of appropriate absorbent systems for blood-based liquids such as menses particularly difficult.

Foams of various types have been suggested for use in tampons, sanitary napkins and other articles that absorb blood and blood-based liquids. See for example U.S. Pat. No. 4,110,276 (DesMarais), issued Aug. 29, 1978 (soft, flexible, open celled foams made from polyurethanes, cellulose, or styrene/butadiene rubber that can be used in tampons and sanitary pads); U.S. Pat. No. 4,752,349 (Gebel), issued Jun. 21, 1988 (foams of "medium cell size" hydrophilized by surfactant treatment and having a density within the range of 0.1 to 0.8 g/cc); U.S. Pat. No. 4,613,543 (Dabi), issued Sep. 28, 1986 (hydrophilic cellular polymers used in catamenial products); U.S. Pat. No. 3,903,232 (Wood et al.), issued Sep. 2, 1975 (compressed hydrophilic polyurethane foams useful in biomedical applications, including catamenial devices); U.S. Pat. No. 4,049,592 (Marans et al.) issued Sep. 20, 1977 (biodegradable hydrophilic polyurethane foams highly absorptive upon contact with liquids or bodily liquids having utility in sanitary napkins and the like). Prior foams used in these products have tended to have relatively large cell sizes. As a result, these prior foams do not exert sufficient fluid capillary pressure for blood and blood-based liquids to acquire discharged menstrual liquids quickly from and through the topsheet of catamenial products such as sanitary napkins. This results in undesirable wetness since the surface in immediate contact with the body retains some of the fluid that is not absorbed into the core and is available to be transferred back onto the body of the wearer.

Suitable absorbent foams for absorbent products have also been made from a High Internal Phase Emulsion (hereafter referred to as a "HIPE"). HIPE foams can provide the fluid capillary pressure necessary to remove most of the menstrual fluid from the body, or topsheet adjacent to the body, thus minimizing wetness. However, it has been found that the residual hydratable salts such as calcium chloride typically present in prior HIPE foams can impair the rapid acquisition blood and blood-based liquids by these foams, and especially the wicking of such liquids within these foams. As noted above, blood and blood-based liquids such as menses are more highly viscous than water and especially urine. The higher viscosity of these liquids is further increased by the presence of these salts. Moreover, prior HIPE foams often had a foam microstructure too small to admit readily the undissolved components of blood and blood-based liquids such as red blood cells.

Exemplary HIPE foam-based structures are described in, for example, U.S. Pat. No. 5,260,345 (DesMarais et al.), issued Nov. 9, 1993 and U.S. Pat. No. 5,268,224 (DesMarais et al), issued Dec. 7, 1993. These absorbent HIPE foams provide desirable urine handling properties, including: (a) relatively good wicking and fluid distribution characteristics to transport fluid away from the initial impingement zone and into the unused balance of the foam structure to allow for subsequent gushes of fluid to be accommodated; and (b) a relatively high storage capacity with a relatively high fluid capacity under load, i.e. under compressive forces. These HIPE absorbent foams are also sufficiently flexible and soft so as to provide a high degree of comfort to the wearer of the absorbent article; some of these foams, such as those described in U.S. Pat. No. 5,387,207 issued Feb. 7, 1995 (Dyer, et al.), can be made relatively thin until subsequently wetted by the absorbed body liquids. See also U.S. Pat. No. 5,147,345 (Young et al), issued Sep. 15, 1992 and U.S. Pat. No. 5,318,554 (Young et al), issued Jun. 7, 1994, which disclose absorbent cores having a fluid acquisition/distribution component that can be a hydrophilic, flexible, open-celled foam such as a melamine-formaldehyde foam (e.g., BASOTECT™ made by BASF), and a fluid storage/redistribution component that is a HIPE-based absorbent foam.

The art has also considered the use of HIPE foams for absorption of blood and blood-based fluids. For example, U.S. Pat. No. 5,849,805, issued to Dyer on Dec. 15, 1998 describes a process for making HIPE foams capable of absorbing blood and blood-based fluids, especially menses. While this patent makes a passing mention of forming a HIPE into a single-piece catamenial pad, there is no description of how such pad formation may be done. In another example, U.S. Pat. No. 5,899,893, issued to Dyer, et al. on May 4, 1999 describes HIPE foam-containing absorbent articles that are particularly suited for absorption of blood and blood-based fluids. However, the absorbent articles described therein are all substantially planar and the HIPE foam is in a sheet form.

A HIPE foam-based absorbent article having tridimensional character is described in U.S. Pat. No. 5,873,869, issued to Hammons, et al. on Feb. 23, 1999 ('869 patent). The article described therein comprises a primary absorbent member in a tube form with a roughly triangular cross section and a secondary absorbent member. The primary absorbent member is assembled from a several sheets of a foam material derived from a HIPE and is sufficiently conformable to, at least partially, fit into a wearer's interlabial space. The use of such HIPE foams in absorbent articles is discussed in greater detail below. While such structures provide desirable conformity, they are complex to assemble because they comprise many components requiring assembly into a functional article.

Other HIPE foams having three dimensionality are also known. For example, U.S. Pat. No. 3,256,219 ('219 patent), issued to Will on Jun. 14, 1966, describes coating a workpiece filling a mold with HIPE foams formulated from monomers such as styrene and styrene derivatives; acrylic and methacrylic acid esters, such as methyl methacrylate; and acrylonitriles. In particular, when using the HIPE in molds, the '219 patent teaches blending the HIPE with a powder or viscous liquid polymer formed from the same monomer used in the HIPE. While such references may teach rudimentary aspects of producing tridimensional articles from HIPEs, there is no teaching of absorbent articles or of absorbent HIPEs. Further, and importantly, there is no teaching of suitable processes for forming three dimensional articles from the HIPEs disclosed therein, of suitable materials for use in a molding process, or of other information enabling one of skill in the art to produce a variety of molded articles that comprise a HIPE foam.

Therefore, it is desirable to provide an absorbent components for absorbent articles, such as sanitary napkins that maintain contact with and conform as closely as possible to the wearer's body. It is further desirable to provide such components in a three dimensional configuration so as to facilitate such contact and conformity. It is still further desirable to produce such components from a foam material, such as a HIPE foam, which is especially suitable for handling, absorbing, and storing blood-based liquids, such as menses while being resilient so that the absorbent article can readily contact and conform to a wearer's body. It is also desirable to produce such three dimensional absorbent foam components using a molding process so that three dimensional shapes matching the complex curvature of a wearer's body can be provided.

It is further desirable to provide other tridimensional products from HIPE foams whereby the particular advantages of the foam composition can provide the article with properties that may be attainable only with difficulty if the article is produced from other materials and to produce such articles using molding processes amenable to high speed commercial production.

These and other aspects of the present invention will be more readily apparent when considered in reference to the following description and when taken in conjunction with the accompanying drawings.

SUMMARY OF THE INVENTION

The present invention is directed to a method of molding a foam material to produce three dimensional articles. Such three dimensional articles are particularly suitable for use as absorbent components in absorbent articles such as sanitary napkins, panty liners, interlabial devices, and adult incontinence pads to provide improved acquisition of blood-based liquids such as menses, and improved fit relative to a female wearer's body. Other tridimensional foam based articles having particularly desirable combinations of foam properties and tridimensionality can also be produced using the method of the present invention.

The method of forming the molded foams used in the present invention allows these absorbent foams to have cells and holes small enough to provide a high capillary absorptive pressure but large enough to prevent or minimize blockage by the insoluble components of these liquids. In particular, the process of forming the molded foams comprises the steps of forming a HIPE wherein the HIPE is a water-in-oil emulsion wherein the oil phase comprises polymerizable monomers that are cured into a HIPE foam having the properties described below. The HIPE is deposited into a mold designed to hold the HIPE in the desired three dimensional configuration for use as an absorbent component while the HIPE cures into a HIPE foam. The molded HIPE foam is then removed from the mold and provided with any desired post molding treatment (e.g., washing and rehydrophilization). If desired, the molded article can be used as is or further converted into a finished article.

When the finished article is an absorbent article, the foam materials used for the absorbent article of the present invention are capable of absorbing blood and blood-based liquids such as menses and then moving these absorbed liquids efficiently to other regions of the foam. These absorbent polymeric foam materials comprise a hydrophilic, flexible, nonionic polymeric foam structure of interconnected open-cells. This foam structure has:

A) a capillary specific surface area in the range of from about 0.0060 to about 0.10 m²/cc;

B) a resistance to compression deflection of from about 5 to about 90% when measured under a confining pressure of 0.74 psi at 31° C. after 15 minutes;

C) a free absorbent capacity of from about 15 to about 125 g/g;

D) less than about 2% of residual hydratable salts.

A particularly important attribute of the foams used in the present invention is that the connecting passages (holes) between the cells of these foams are sufficiently large to pass insoluble solids such as erythrocytes (mean diameter greater than about 8 $\mu$m). As a result, these holes do not become blocked or obstructed by blood and blood-based liquids absorbed by the foam. Even though the cells and holes are large enough to allow free movement of insoluble components in blood and blood-based liquids, they are sufficiently small so as to produce the necessary high capillary absorption pressure required of absorbents used in catamenial products. In other words, these foams combine high capillary absorption pressure with sufficient openness to allow free movement of the insoluble components in blood and blood-based liquids such as menses. Typically, the cells of these foams have a number average cell size of from about 20 to about 2500 $\mu$m, while the holes be tween these cells have a number average hole size of from about 5 $\mu$m to about 60 $\mu$m.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings in which:

FIG. 2 is a longitudinal cross-sectional view of the sanitary napkin shown in FIG. 1.

FIG. 3 is a cross sectional view of an alternative embodiment of a sanitary napkin having a core made using the method of the present invention.

FIG. 4 is a perspective view of a curvilinear molded tridimensional HIPE foam formed according to the method of the present invention.

DETAILED DESCRIPTION OF THE INVENTION

I . Definitions

The term "use", as used herein, refers to the period of time that starts when the absorbent article is actually put in contact with the anatomy of the user.

The terms "joined" or "affixed", as used herein, encompasses configurations whereby a first member is directly connected to a second member and configurations whereby a first member is indirectly connected to a second member by connecting the first member to intermediate members which in turn are connected to the second member.

As used herein, the term "pudendal" refers to the externally visible female genitalia and is limited to the labia majora, the labia minora, the clitoris, and the vestibule.

2. Three Dimensional Structures a. General Characteristics of a Preferred Embodiment of a Three Dimensional Absorbent Article of the Present Invention In one aspect, the present invention is directed to absorbent articles for wearing by a human female such as sanitary napkins, panty liners, interlabial devices, tampons, and adult incontinence pads. The absorbent articles of the present invention have a molded tridimensional foam absorbent structure that provides improved acquisition of blood-based liquids such as menses, and improved fit relative to a female wearer's body.

In the simplest configuration (not shown), an absorbent article according to the present invention only comprises a molded tridimensional absorbent structure. As will be recognized, a molding process can be provided, or the molded absorbent structure treated to provide functionalities typically provided by separate components in prior art absorbent structures. That is, components such as a topsheet and a backsheet are optional in such a simple embodiment. Topsheet functionality can be provided by molding the structure having a body contacting surface with a cell size distribution and mechanical properties having topsheet functionality and an internal portion, with a different cell size distribution that provides storage functionality (Such a molding process is discussed below). The absorbent structure can also be molded so as to provide a "skin" on a garment contacting to provide backsheet functionality or the garment surface can be treated so as to be substantially impermeable to aqueous fluids (e.g., by a fluorocarbon treatment).

Figure 1:
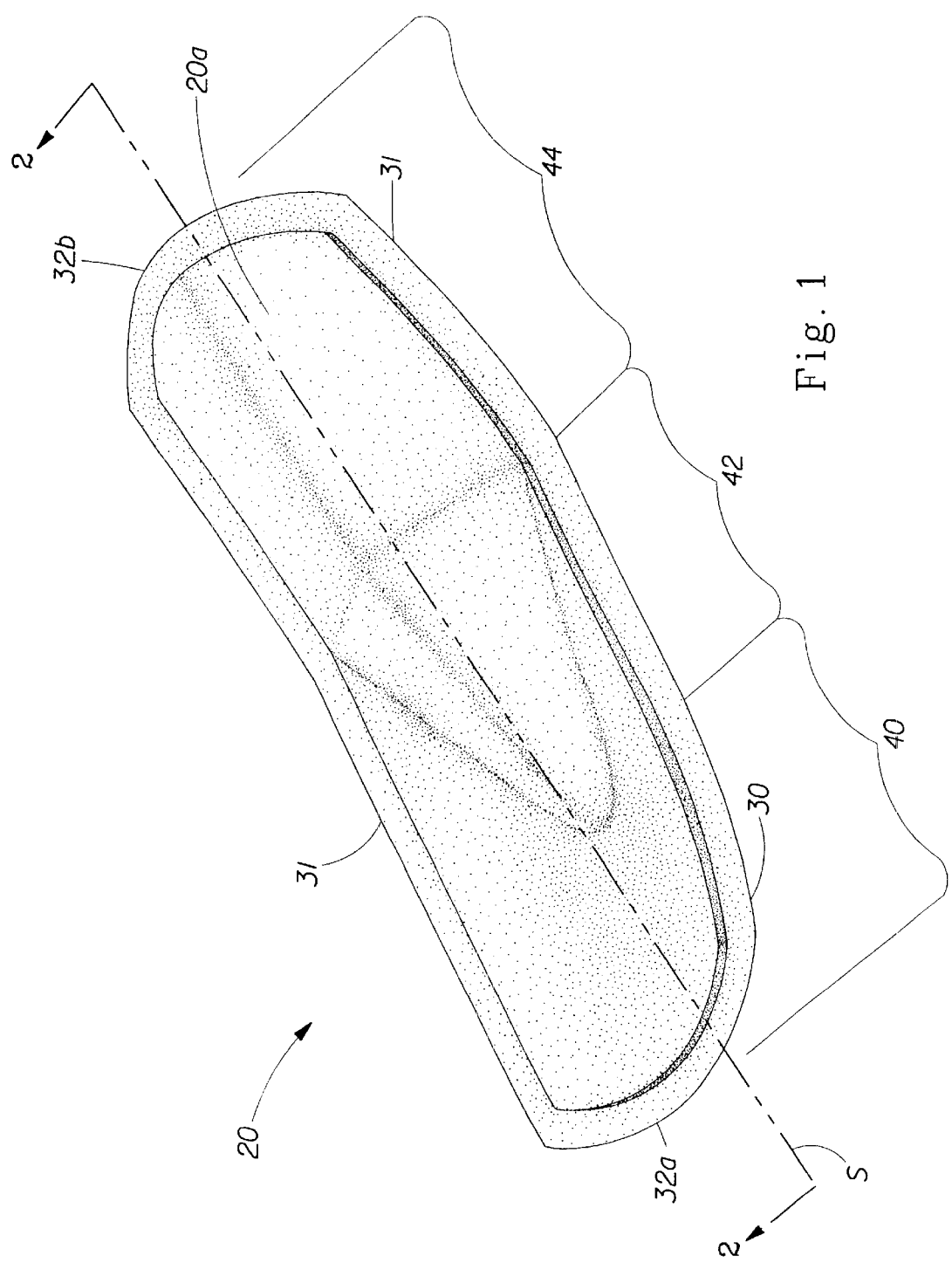
FIG. 1 is a perspective view of a tridimensional sanitary napkin having a core made using the method of the present invention.

FIG. 1 is a perspective view of a more conventional sanitary napkin 20 of the present invention with its tridimensional structure, with most of the portion of the sanitary napkin 20 that faces or contacts the wearer, oriented towards the viewer. The design of sanitary napkin 20 is similar to the three dimensional sanitary napkin described in the aforementioned '095 application. As noted in the discussion above, such a device provides good contact with the anatomy of a female wearer. While it is recognized that improvements, such as providing curvilinear contact surfaces, can be made to provide further improvements in body contact, the device described in the '095 application will be used to demonstrate the principles of the present invention. In particular, the process-related aspects of the present invention (see discussion below) can be readily illustrated thereby.

The sanitary napkin 20 shown in FIGS. 1 and 2 can be of any suitable size. Preferably, the embodiment of the sanitary napkin 20 shown in the drawings is of a size sufficient so that it is able to cover the maximum area of a wearer's panties to reduce or eliminate soiling of the same by the wearer's bodily fluids, particularly for night time usage. In one preferred embodiment, sanitary napkin 20 is about 8 cm wide at its narrowest point and approximately 22 cm in length measured along the longitudinal centerline L. In another embodiment, the width of the sanitary napkin 20 is the same, but the length ranges from about 30 cm to about 35 cm. In other, more conventionally-sized embodiments, such as those intended for day time use, sanitary napkin 20 is preferably from about 20 to 40 cm long, more preferably from about 22 to 35 cm long, and most preferably is about 24 cm long. Sanitary napkin 20 is preferably from about 5 to 15 cm in width, more preferably from about 5 to 10 cm in width, and most preferably from about 5 to 8 cm in width.

The overall sanitary napkin 20 for embodiments such as those shown in the drawings, preferably ranges in height from about 5 mm to a maximum of between about 30 to 40 mm in its uncompressed state. In other embodiments, such as embodiments designed for use in Japan where the sanitary napkin is held closer to the wearer's body by menstrual shorts, the height does not need to even be this great to provide a certain amount of body contact.

As better shown in FIG. 2, the sanitary napkin 20 comprises a liquid pervious topsheet 22, a liquid impervious backsheet 23 joined to the topsheet 22, and an absorbent core 24 positioned between the topsheet 22 and the backsheet 23.

The sanitary napkin 20 has two surfaces, a body facing or contacting surface 20a and a garment facing or contacting surface 20b. The body contacting surface 20a is intended to be worn adjacent to the body of the wearer while the garment surface 20b is on the opposite side and is intended to be directed towards the undergarment when the sanitary napkin 20 is worn, e.g. placed against it. Corresponding body facing and garment facing surfaces can also be identified in each single layer that constitutes the sanitary napkin 20 e.g., in the absorbent core 24. The sanitary napkin 20 has a longitudinal symmetry plane S. The term "longitudinal", as used herein, refers to a line, axis or direction in the sanitary napkin 20 that is generally aligned with (e.g., approximately parallel to) a vertical plane which bisects a standing wearer into left and right body halves when the sanitary napkin 20 is worn. The symmetry plane S of the sanitary napkin 20 substantially corresponds to this vertical plane that bisects the standing wearer. While it is preferred that the sanitary napkin 20 is exactly divided by the longitudinal symmetry plane S into two symmetrically equal halves, it is also possible that the two halves are not symmetric. The term "transverse", as used herein, refers to a direction that is generally perpendicular to the longitudinal symmetry plane S. The term "longitudinally oriented" refers to a direction, as seen in plan view, comprised within ±45 degrees, of the longitudinal symmetry plane S; the term "transversely oriented" similarly refers to any other direction, as seen in plan view.

The terms "front" and "rear", as used herein, refer to portions or edges in the sanitary napkin 20 that are oriented towards the front and rear part of the wearer's body, respectively, when the sanitary napkin 20 is being worn.

The sanitary napkin 20 has a periphery 30, that is defined by the outer edges of the sanitary napkin 20. The longitudinal edges 31 of the sanitary napkin 20 are aligned with the longitudinal symmetry plane S, and the ends edges of the sanitary napkin 20 comprise a front end edge 32a and a rear end edge 32b. The absorbent core 24 of the sanitary napkin has a front portion 40, a central portion 42 and a rear portion 44, each one preferably corresponding to approximately one third of the total length of the absorbent core 24. Corresponding front, central and rear portions can be respectively identified in the sanitary napkin 20 also.

The sanitary napkin 20 of the present invention is tridimensional since it is provided prior to use with a tridimensional structure that is intended to conform to the complex body shapes of the female pudendal region. The tridimensional sanitary napkin 20 of the present invention preferably has a substantially constant thickness, that is more preferably less than 5 mm; the sanitary napkin can be therefore considered to be of the thin type.

While the topsheet, the backsheet, and the absorbent core may be assembled in a variety of well known configurations (including so called "tube" products or side flap products), FIG. 1 shows a preferred embodiment of the sanitary napkin 20 in which the topsheet 22 and the backsheet 23 have length and width dimensions generally larger than those of the absorbent core 24. The topsheet 22 and the backsheet 23 extend beyond the edges of the absorbent core 24 to thereby form the periphery 30 of the sanitary napkin 20.

The topsheet 22 is compliant, soft feeling, and non-irritating to the wearer's skin. Further, the topsheet 22 is liquid pervious, permitting liquid (e.g., menses and/or urine) to readily penetrate through its thickness. A suitable topsheet 22 may be manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibres (e.g., wood or cotton fibers), synthetic fibres (e.g., polymeric fibres such as polyester, polypropylene, or polyethylene fibres); or from a combination of natural and synthetic fibres.

A preferred topsheet comprises an apertured formed film. Apertured formed films are preferred for the topsheet because they are pervious to body fluids and yet non-absorbent and have a reduced tendency to allow liquids to pass back through and rewet the wearer's skin. Thus, the surface of the formed film which is in contact with the body remains dry, thereby reducing body soiling and creating a more comfortable feel for the wearer.

Suitable formed films are described in U.S. Pat. No. 3,929,135, issued to Thompson on Dec. 30, 1975; U.S. Pat. No. 4,324,246, issued to Mullane, et al. on Apr. 13, 1982; U.S. Pat. No. 4,342,314, issued to Radel, et al. on Aug. 3, 1982; U.S. Pat. No. 4,463,045, issued to Ahr, et al. on Jul. 31, 1984; and U.S. Pat. No. 5,006,394, issued to Baird on Apr. 9, 1991. A preferred topsheet for the absorbent article of the present invention is a formed film described in one or more of the above patents and marketed on sanitary napkins by The Procter & Gamble Company of Cincinnati, Ohio as "DRI-WEAVE". Such formed film topsheets can also be treated with hydrophobic materials to provide a surface energy gradient facilitating flow of deposited fluids away from the body surface 20a of sanitary napkin 20 as is described in U.S. patent application Ser. No. 08/826,508, filed in the name of Ouellette, et al. on Apr. 11, 1997.

In a preferred embodiment of the present invention, the body or exposed surface of the formed film topsheet is hydrophilic so as to help liquid transfer through the topsheet faster than if the body surface were not hydrophilic so as to diminish the likelihood that menstrual fluid will flow off the topsheet rather than flowing into and being absorbed by the absorbent core. In a preferred embodiment, surfactant is incorporated into the polymeric materials of the formed film topsheet such as is described in US Statutory Invention Registration H1670, issued in the name of Aziz, et al. on Jul. 1, 1997. Alternatively, the body surface of the topsheet can be made hydrophilic by treating it with a surfactant such as is described in U.S. Pat. No. 4,950,264, issued to Osborn on Aug. 21, 1990.

The absorbent core 24 used in the sanitary napkin 20 of the present invention acquires, absorbs, and contains body exudates. The absorbent core 24 also provides a tridimensional shape to sanitary napkin 20 so that the sanitary napkin 20 conforms to the shape of a wearer's body. Thus, the absorbent core 24 is preferably capable of absorbing and containing body exudates, and is compressible, conformable, resilient, and non-irritating to the wearer's skin. Preferably, absorbent core 24 comprises a HIPE foam material as discussed below.

Absorbent core 24 provides a structural tridimensional shape to sanitary napkin 20. As used herein the term "structural tridimensionality" incorporates not only those structures that cannot be achieved by simply folding or pleating an initially flat article, but also tridimensional structures that can be formed by such operations (It should be noted that the process of forming or pleating an inherently flat article inherently creates stress lines at the bends that can interfere with performance requirements, such as fluid handling while molding the same shape does not create similar potential regions of reduced performance). As noted above, such tridimensionality allows improved conformity to the shape of a human female pudendal region. As will be discussed below, the tridimensional absorbent core 24 can advantageously be produced by molding a HIPE and polymerizing the HIPE in the mold to provide a shaped HIPE foam having the predetermined tridimensional structure shown in FIGS. 1 and 2. As will be recognized, many such predetermined shaped absorbent core designs may be produced by such molding processes.

The total absorbent capacity of the absorbent core 24 should be compatible with the intended exudate loading for the sanitary napkin 20. Sanitary napkin 20 preferably has a capacity equal to, and more preferably, greater than at least the lower end of the range of capacities of the sanitary napkins described in U.S. Pat. Nos. 4,950,264 and 5,009,653 issued to Osborn. Sanitary napkin 20 may, for example, have a total capacity of between about 20–60 grams of sterile saline measured according to the procedure set out in U.S. Pat. No. 5,009,653 issued to Osborn. Further, the absorbent capacity of the absorbent core 24 may be varied to accommodate wearers ranging in the expected amount of exudate fluid volume. For instance, a different absorbent capacity may be utilized for sanitary napkins intended for day time use as compared with those intended for night time use, or for sanitary napkins intended for use by teenage females as compared with those intended by more mature women.

In the embodiment shown in FIGS. 1 and 2, the absorbent core 24 has a uniform set of properties that provide the desired absorbency, resiliency and other needed characteristics to sanitary napkin 20. As noted above, and discussed in greater detail below, such characteristics are particularly advantageously provided by HIPE foams.

The HIPE foam materials selected for use as the absorbent core 24 are preferably compliant, soft, comfortable, compressible, and resilient to enhance body fit and comfort of the sanitary napkin 20. Preferably, the absorbent core 24 is compressible so that sanitary napkin 20 will deform under relatively small forces exerted in the female pudendal region that are experienced during normal use. In addition to being compressible, the foam materials comprising the absorbent core 24 are preferably conformable so that the sanitary napkin 20 is able to provide improved fit into and around the labia and perineum. It is also important that the sanitary napkin 20 be sufficiently resilient such that when subjected to normal wearing forces it does not permanently collapse. The absorbent core 24 provides the sanitary napkin 20 with the desired resilient characteristics so that the sanitary napkin 20 conforms to the contours of the body to provide intimate contact with the exposed genitalia of the female user. Intimate contact with the exposed female genitalia helps provide better transfer of liquid exudates from the user into the sanitary napkin 20 without allowing such liquids to bypass and/or run-off the sanitary napkin 20. While the resilient characteristics of the absorbent core 24 allow for improved fit, they must be balanced against the need for the product to be both soft and comfortable for the wearer.

Similarly, the absorbent core 24 must be sufficiently resilient that capillary forces do not cause the cells therein to collapse. Again, this results in a balance between softness and fluid handling properties. In an embodiment, not shown in the drawings, absorbent core 24 comprises two main portions, an acquisition portion and a storage portion. The acquisition portion is the portion of the absorbent core 24 that has desirable softness and conformability (with the resulting increased risk of capillary collapse) while being particularly suited for providing the absorbent core 24 with the ability to rapidly absorb bodily exudates from the wearer's body immediately upon discharge therefrom. The acquisition portion comprises a hydrophilic, flexible, non-ionic polymeric foam structure of interconnected open cells which is capable of absorbing blood and blood-based liquids. The foam structure forming the acquisition portion has cells within the foam structure that are of a size within a first range of values (or first average cell diameter or "cell size").

The storage portion is the portion of the absorbent core 24 that is particularly suited for obtaining bodily exudates, especially menses, from the acquisition portion, and permanently storing such exudates (capillary collapse resistance is of importance in facilitating permanent storage). The storage portion preferably also comprises a hydrophilic, flexible, nonionic polymeric foam structure of interconnected open cells which is capable of absorbing blood and blood-based liquids. The foam structure forming the storage portion has a foam structure have a second cell size (or second average cell diameter or "cell size").

Preferably, the acquisition portion and the storage portion are provided with different properties. The acquisition portion and the storage portion may differ in size, the type of foam used, the cell size of the foam, the resistance to compression of the foam, and absorbent capacity, to list a few possible differences. The different properties are preferred since the storage portion should be able to take liquids from the acquisition portion, to store those liquids, and need not be in as close contact with the wearer's body as the acquisition portion. The acquisition portion preferably has softer mechanical properties which may be achieved by virtue of a lower Tg, higher W:O ratio, lower cross-linker levels, or a combination of such properties accompanied by a coarser cellular microstructure as compared with the storage portion (See below for further discussion of the properties of HIPE foams.).

Depending on the desired design for absorbent core 24, the acquisition portion and the storage portion may have a wide variety of spatial relationships with respect to each other. For example, the acquisition portion and the storage portion may be in a layered relationship with respect to each other wherein the acquisition portion lies immediately beneath the topsheet 22 (or secondary topsheet) and the storage portion lies between the acquisition portion and the backsheet 23. The acquisition portion and the storage portion may also be in a side-by-side relationship wherein some of the capacity of the storage portion is disposed laterally outboard of the acquisition portion. Processes for molding such structures for absorbent core 24 can take particular advantage of the process for producing heterogeneous foam materials that is described in U.S. Pat. No. 5,856,366, issued to Shiveley, et al. on Jan. 5, 1999.

The backsheet 23 of sanitary napkin 20 is preferably impervious to liquids (e.g., menses and/or urine) and is preferably manufactured from a thin plastic film, although other flexible liquid impervious materials may also be used. As used herein, the term "flexible" refers to materials which are compliant and will readily conform to the general shape and contours of the human body. In use, the backsheet 23 is interposed between the absorbent core 24 and the user's undergarments. The function of the backsheet 23 is to prevent exudates which may be expelled from or which inadvertently bypass the absorbent core 24 and exudates absorbed and contained in the absorbent core 24 from contacting and soiling the user's undergarments.

The backsheet 23 may comprise a woven or nonwoven material, polymeric films such as thermoplastic films of polyethylene or polypropylene, or composite materials such as a film-coated nonwoven material. Preferably, the backsheet is a polyethylene film having a thickness of from about 0.012 mm (0.5 mil) to about 0.015 mm (2.0 mil). Exemplary polyethylene films are manufactured by Clopay Corporation of Cincinnati, Ohio under the designation P18-0401 and Microflex 1401. The backsheet is preferably embossed and/or matte finished to provide a more clothlike appearance. Further, the backsheet may permit vapors to escape from the absorbent core 24 (i.e., breathable) while still preventing exudates from passing through the backsheet.

The topsheet 22, the backsheet 23, and the absorbent core 24 may be assembled in a variety of configurations known in the art (including so called "sandwich" products and "tube" products). Several preferred sanitary napkin configurations and features that the sanitary napkin can be provided with are described generally in the following patents: U.S. Pat. No. 4,321,924, issued to Ahr on Mar. 30, 1982; U.S. Pat. No. 4,425,130 issued to DesMarias on Jan. 10, 1984; U.S. Pat. Nos. 4,950,264 and 5,009,653, both issued to Osborn on Aug. 21, 1990 and Apr. 23, 1991, respectively; and U.S. Pat. Nos. 5,234,422 and 5,308,346 issued to Sneller, et al.

The components of sanitary napkin 20 shown in FIGS. 1 and 2 are preferably assembled in a sandwich construction in which the topsheet 22 and the backsheet 23 have dimensions that are generally larger than those of the absorbent core 24. If an optional secondary topsheet or acquisition layer (not shown) is used, it is disposed between the topsheet 22 and the absorbent core 24 and joined to one or both of the elements. The topsheet 22 is joined to the backsheet 23 in the region of the sanitary napkin that lies outboard of the absorbent core 24. Preferably, the topsheet 22 is joined to these components by a core bonding adhesive that is applied in a spiral pattern. The absorbent core 24 is preferably joined to the backsheet 23. Preferably, the absorbent core 24 and the backsheet 23 are joined using a core integrity adhesive applied in a plurality of strips of adhesive, each of which comprises spirals of adhesive. Exemplary means for joining these components of sanitary napkin 20 comprises several lines of adhesive filaments swirled into a spiral pattern such as illustrated by the apparatus and method shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. The core integrity adhesive can be applied over the entire garment facing side of the secondary absorbent, over the whole product width (including the extensions of the backsheet that will lie beyond the edges of the absorbent core 24) or any portion thereof. Preferably, the core integrity adhesive is applied to the entire interface between the garment facing side of the topsheet 22 and the backsheet 23.

b. Alternative Three Dimensional Absorbent Structures

FIG. 3 shows one alternative embodiment of a three dimensional sanitary napkin of the present invention, in the form of a compound sanitary napkin 320 that is preferred for night time use. Compound sanitary napkin 320 is similar to sanitary napkin 20 shown in the '869 patent. As shown in FIG. 3, the sanitary napkin 320 basically comprises a main body portion 322 and two side extensions or side wrapping elements 324. The main body portion 322 of the sanitary napkin 320 comprises a primary absorbent member (or "primary absorbent component" or "core tube") 340 and a secondary absorbent member (or "secondary absorbent component" or "base pad") 360 that are joined together by union means 370. The three dimensional, molded foam structures of the present invention are particularly suitable for use as a primary absorbent member 340 because of the desirable combination of absorbent properties and resiliency. For example, the layered core 50 of the '869 patent could be replaced by the prismatic (triangular cross section) molded absorbent core 350 shown in FIG. 3 with resulting simplification to the structure.

Because core 350 comprises a molded HIPE foam that can be produced using the method discussed below, the core has a tridimensional shape while being both absorbent and resilient. In particular, the absorbent core 350 can be of a size and compressibility that at least a portion of the sanitary napkin 320 will fit comfortably within and fill the space between a wearer's labia majora without deforming the wearer's labia majora so that the sanitary napkin 320 will be molded by the wearer's labia majora and conform to the shape thereof in the front portion of the sanitary napkin 320, and substantially fill the gluteal groove (or crevice between the wearer's buttocks) in the rear. In order to do this, the absorbent core 350 can be provided with a fairly high amount of bulk. However, due to the compressibility and conformability of the HIPE foam material, even though it is bulky, it is very comfortable for the wearer.

FIG. 4 shows a curvilinear molded shape that is suitable for use as an absorbent core. As noted above, the sanitary napkin 20 while being suitable for demonstrating the principles of the molding method of the present invention, can be improved by, being made more curvilinear. Absorbent member 420 shown in FIG. 4 is such a structure. In particular, the molding process of the present invention facilitates formation of ridge 430 that, at least partially, penetrates into a wearer's interlabial space to more readily intercept menses as it exits the vaginal orifice. Absorbent member 420 comprises a HIPE foam material so it is particularly comfortable to a wearer when used as part of an absorbent article (see discussion above). As will be discussed below, the method of the present invention envisions steps that permit absorbent member 420 to comprise HIPE foam materials with differing properties. For example, absorbent member 420 can comprise an internal portion (not shown) of a HIPE foam having properties particularly useful for storage (relatively small cell size and stiffer) and an external portion (particularly a portion of ridge 430) comprising a HIPE foam with properties particularly suited for acquisition and comfort (larger cell size and softer foam).

The present invention also comprises absorbent tampons having a tridimensional structure (not shown). Such tridimensional tampons are particularly desirable because they can be shaped and sized so as to more intimately conform to the interior shape of the vaginal cavity than prior art tampons. Forming such tridimensional tampons from a HIPE foam is particularly desirable because a shaped structure having relatively large expanded dimensions can be compressed to a size that is small enough to readily fit into a conventionally sized (or even smaller) tampon inserter because of the low density of HIPE foams.

c. Other Three Dimensional Molded Shapes

As will be recognized, the molded three dimensional HIPE foams of the present invention can be used to produce a multiplicity of three dimensional shapes. Exemplary implements are described in more detail in copending provisional U.S. patent application Ser. No. 60/163,064, filed in the name of Dyer, et al. on Nov. 2, 1999 (P&G Case No. 7849P). Exemplary implements are discussed in the following paragraphs. All can be made in a particularly effective manner using the molding processes discussed below.

Toys

HIPE foams can serve as functioning implements in a variety of toys and entertainment/educational articles for children. The surface may be provided with a specific shape, for example, of an animal or other irregular figure, to which ink is applied. The HIPE foam absorbs the ink and serves as an effective stamp for replicating the shape on paper or on a game board (as for tracking one's progress around the game board resulting from, for example, the throw of dice). The HIPE foam may be formed into intricate blocks to serve as building blocks, similar to the system described in U.S. Pat. No. 5,916,006 (Ganson) issued Jun. 29, 1999. The HIPE foam blocks may be compressed readily and stored in that state while recovering to the original state shortly after being liberated from the storage vessel. This minimizes the storage area required for the blocks. HIPE foam can serve as a storage vessel for water which will release the water when compressed, as for example the foam may be molded into a spherically shaped article to serve as projectile devices which may further be saturated with water or colored water. These spheres may be thrown or otherwise propelled as part of a game at other participants. The softness of the spheres prevents injury to the participants being hit. The HIPE foam may be shaped into wicking strips which may be immersed in colored water to illustrate the wicking property of these foams. The wicking strips, for example, may be placed several together in an arc which simulates formation of a rainbow when immersed in several different colored water solutions.

Insulation

Similarly, the low density of HIPE foams makes them particularly useful as an insulation material. (See, for example, U.S. Pat. No. 5,633,291 (Dyer et al.) issued May 27, 1997 and U.S. Pat. No. 5,770,634 (Dyer et al.) issued Jun. 23, 1998.) When a three dimensional structure has particular utility as an insulation material, the molding process discussed herein is particularly useful as a means of producing such elements.

3. HIPE- Derived Foams a. General Properties

Absorbent Foams

The overall characteristics of HIPE foams suitable for use in the molded three dimensional absorbent articles according to the present invention will now be examined. Depending on particular needs for absorbent articles all portions of the core 24 can comprise the same type of foam or different portions can comprise different types of foam. Preferably, all portions of core 24 comprise similar foam compositions. While all portions may comprise the same basic foam composition, certain properties (e.g., cell size) may be varied as desired to meet performance requirements.

The foams used in the absorbent structure of the present invention are open-celled polymeric foams. For purposes of the present invention, a foam material is "open-celled" if at least 80% of the cells in the foam structure that are at least 1 μm size are in liquid communication with at least one adjacent cell. The foams used in the foam absorbent core 24 of the present invention preferably have a number average cell size of from about 30 to about 250 μm. The cells in such substantially open-celled foam structures have intercellular openings or holes that provide passageways large enough to permit free and ready movement of blood and blood-based liquids, such as menses, from one cell to another within the foam structure, even though these liquids contain certain insoluble components. These substantially open-celled foam structures will generally have a reticulated character with the individual cells being defined by a plurality of mutually connected, three dimensionally branched struts. Cell size is a foam parameter that can impact a number of important mechanical and performance features of the absorbent foams used in the present invention. Cell size contributes to capillary suction specific surface area (CSSA), together with foam hydrophilicity, determines the capillarity of the foam. Therefore, cell size is a foam structure parameter that can directly affect the fluid wicking properties of absorbent foams, as well as the capillary pressure that is developed within the foam structure. A number of techniques are available for determining the cell size of foams. The most useful technique for determining cell size in foams involves a simple measurement based on the scanning electron photomicrograph of a foam sample. Superimposing a scale on a photomicrograph of the foam structure can be used to determine average cell size via visual inspection or an image analysis procedure. Foam cells, and especially cells that are formed by polymerizing a monomer-containing oil phase that surrounds relatively monomer-free water-phase droplets, will frequently be substantially spherical in shape. The size or "diameter" of such spherical cells is a commonly used parameter for characterizing foams in general. Since cells in a given sample of polymeric foam will not necessarily be of approximately the same size, an average cell size, i.e., number average cell diameter, will often be specified.

The cell size of HIPE foams for acquisition is preferably greater than that of the foam comprising for storage. Preferably, the cell size for acquisition foam (expressed in terms of number average cell diameter or mean cell diameter) ranges between about 100 and about 250 microns and the cell size for storage preferably ranges between about 20 to about 100 microns. The larger cell size provides the acquisition foam with the ability to acquire blood-based liquids at a higher rate by allowing red blood cells, debris, and other liquids to be taken up. The difference in cell size between an acquisition foam and a storage foam can establish a capillary gradient from the acquisition to the storage foams when both materials are a component of an absorbent core such as core 24. This will cause liquids to move from the acquisition portion into the storage portion. The movement of liquids out of the acquisition portion will drain the acquisition portion to make room in the acquisition portion for subsequent loading of liquids. In addition, the capillary gradient will also ensure that liquids which are transported to the storage portion will remain in the storage portion, and will not tend to go back up into the acquisition portion. The storage portion develops higher capillary pressure, but will generally accept menstrual liquids at a slower rate than the acquisition portion.

Another feature useful in defining these preferred foams is hole size. The holes are the openings between adjacent cells that maintain liquid communication between these cells. The foams used in the present invention have hole sizes sufficiently large to allow passage of the insoluble components of blood, especially the red blood cells, to avoid blockage of these liquid passages. The preferred technique for determining hole size is image analysis based on scanning electron micrographs of the foams as discussed above. Depending on intended use, the foams used in the present invention various ranges for number average hole size. For example, a foam for acquisition will suitably have cells ranging between about 20 m and about 60 $\mu$m, preferably between about 30 $\mu$m and about 50 $\mu$m. Storage material has smaller cells with an average size between about 5 $\mu$m to about 40 $\mu$m, and preferably from about 10 to about 30 $\mu$m. As will be recognized, foams intended for use as an acquisition component generally have larger cells than foams intended for storage.

It may also be more desirable and preferable to alternatively express the difference in the foam properties of an acquisition portion and a storage portion in terms of "capillary specific surface area" ("CSSA") since such a measurement may more accurately correlate with the liquid handling properties when two such portions are used in a core such as absorbent core 24. The capillary specific surface area is one of a number of characteristics important to absorbing and transporting blood and blood-based liquids. "Capillary specific surface area" is a measure of the test-liquid-accessible surface area of the polymeric network accessible to a test liquid. Capillary specific surface area is determined both by the dimensions of the cellular units in the foam and by the density of the polymer comprising the foam. It is, thus, a way of quantifying the total amount of solid surface provided by the foam network to the extent that such a surface participates in absorbency. The capillary specific surface area is determined by the method set forth in the TEST METHODS section of U.S. Pat. No. 5,387,207 issued to Dyer, et al. on Feb. 7, 1995 and is expressed in units of $m^2$/cubic centimeter.

Generally, the CSSA of the foam at a constant volume increases as the cellular structure becomes smaller celled (or "finer"). Higher surface areas are highly desirable to develop the capillary pressure needed to attract liquids such as menses away from the body. However, the surface area of the foam can reach the point that the rate of liquid absorption becomes limiting, as well as increasing the likelihood that insoluble components within the liquid can no longer pass readily from one cell to another. Accordingly, the surface area of the foam needs to be selected within a particular range to balance these competing factors. Polymeric foams that are useful in the foam absorbent core of the present invention are those that have a capillary specific surface area in the range of from about 0.0060 to about 0.10 $m^2$/cc. Typically, the capillary specific surface area is in the range from about 0.010 to about 0.030 $m^2$/cc, preferably from about 0.008 to about 0.04 $m^2$/cc.

An acquisition portion of a multi portion core preferably has a lower capillary specific surface area than a storage portion. For example, the acquisition portion may have a CSSA of from about 0.008 to about 0.020 $m^2$/cc. The storage portion may have a capillary suction specific surface area, for example, of from about 0.020 to about 0.03 $m^2$/cc. In this way, the storage portion will have a higher capillary pressure, allowing it to drain liquids from the acquisition portion, thus keeping the body of the wearer relatively free from contact with liquids.

The foams must be suitably resistant to deformation or compression by forces encountered when such absorbent foams are engaged in the absorption and retention of liquids. The resistance to compression deflection (or "RTCD") exhibited by the polymeric foams used in the present invention can be quantified by determining the amount of strain (percentage of uncompressed height) produced in a sample of saturated foam held under a certain pressure for a specified period of time. The method for carrying out this particular type of test is described in the TEST METHODS section of U.S. Pat. No. 5,387,207, issued to Dyer, et al. Foams useful as absorbent members for catamenial products are those which exhibit a RTCD such that a confining pressure of 0.74 psi (5.1 kPa) at 31° C. after 15 minutes produces a strain of typically from about 5 to about 85% compression of the foam structure.

In order for at least a portion of the absorbent core 24 to compress to fit comfortably in the space between the wearer's labia and gluteal groove. It is estimated that the core 24 will not uncomfortably deform the wearer's labia if it has a RTCD that is between about 60% and about 80%. For multi portion cores the acquisition portion should have the same RTCD but a storage portion does not need to be as compressible if it is not in as close proximity to the wearer's body. In addition, providing a higher resistance to compression to a storage portion reduces any tendency for liquids to be "squeezed" out of the storage portion. The acquisition portion may, for example, have a RTCD of between about 60% to about 90%, and more preferably between about 75% to about 85%. The storage portion may, in such a case, have a RTCD of between about 5% to about 75%, and more preferably between about 35% to about 70%.

The foams used in the absorbent structure are preferably also sufficiently resilient so that they do not permanently collapse during use. This will ensure that the foams are able to continue to absorb bodily exudates throughout a wear cycle. The resilient characteristics of the foams also helps ensure that the primary absorbent component will be capable of continuing to conform to and fill the space between the wearer's labia and gluteal groove after initial compression and after changes in the configuration of these parts of the wearer's body caused by body movements. Preferably, the foams used in the absorbent structure will return to at least about 70% of their uncompressed height, more preferably at least about 80%, and most preferably at least about 90% after the removal of the compressive forces.

Another important property of absorbent foams used in the present invention is their free absorbent capacity. For absorbent members useful in catamenial products, free absorbent capacity is the total amount of test liquid (i.e., synthetic urine) that a given foam sample will absorb at equilibrium into its cellular structure per unit mass of solid material in the sample. The foams that are especially useful as absorbent members in catamenial products will at least meet a minimum free absorbent capacity. The free absorbent capacity of the foams used in the present invention can be determined using the procedure described in the TEST METHODS section of U.S. Pat. No. 5,387,207 issued to Dyer, et al. To be especially useful as absorbent members for catamenial products, the foams used in the present invention should have a free absorbent capacity of from about 15 to about 125 g/g, preferably from about 20 to about 50 g/g, and most preferably about 25 g/g, of synthetic urine per gram of dry foam.

It should be understood that these foams can have different properties, features and/or characteristics at different times prior to contact between the foam and the blood or blood-based liquid to be absorbed. For example, during their manufacture, shipping, storage, etc., these foams can have density and/or cell size values outside the ranges set forth hereafter for these parameters, for example if they are stored in a compressed state by packaging. However, such foams are nevertheless still within the scope of this invention if they later undergo physical changes so that they have the requisite values specified hereafter for these properties, features and/or characteristics at least some point prior to and/or during contact with the blood or blood-based liquid to be absorbed.

Other HIPE Foams

The specific foam properties that are suitable for HIPE foams intended for uses other than in an absorbent article will depend on the particular use that is envisioned. For example a cell size for implements, such as the toys discussed above between about 30 μm and about 80 μm is typically optimal. The ultimate end use will also determine whether the HIPE foam is intentionally made hydrophilic (the HIPE foams of the present invention are inherently hydrophobic and are made hydrophilic either by treatment with salts or with surfactants). A key parameter of these foams is their glass transition temperature (Tg) because it is an indicator of foam stiffness at room temperature (Suitably Tg will be between about −40° and about 50° C. For implements or regions within an implement requiring relatively high stiffness, the preferred HIPE foams will have a Tg of from about 20° to about 50° C. For implements regions within an implement wherein flexibility is preferred, HIPE foams which have a Tg between about −40° and about 20° C. will generally be preferred. As is known Tg is substantially determined by the monomer blend that is polymerized to provide the HIPE foam.).

b. Preparation of a Polymeric Foam

A. Overview

The process for preparing the polymeric foam according to the method of the present invention involves the steps of: 1) forming a specific type of stable high internal phase water-in-oil emulsion (or HIPE) having a relatively small amount of an oil phase and a relatively greater amount of a water phase; 2) polymerizing/curing this stable emulsion in a mold under conditions suitable for forming a solid water-filled polymeric foam structure; 3) removing the water-filled polymeric foam from the mold and then washing the foam to remove the original residual water phase, and the residual hydratable salts, if necessary for specific performance requirements, such as use in an article for absorbing blood-based fluids, from the polymeric foam structure; 4) treating the polymeric foam structure with a hydrophilizing solution of surfactant and salt; and thereafter dewatering this polymeric foam structure.

The first step is forming a specific type of stable high internal phase water-in-oil emulsion (or HIPE) having a relatively small amount of an oil phase and a relatively greater amount of a water phase. The water-in-oil emulsion is formed from an oil phase and a water phase. The oil phase comprises from about 85 to about 98% by weight of a monomer component and from about 2 to about 15% by weight of an emulsifier component. The monomer component is capable of forming a copolymer having a Tg of about 50° C. or lower. The "Tg" of a copolymer is its glass transition temperature. The emulsifier component is soluble in the oil phase and is suitable for forming a stable water-in-oil emulsion. The water phase comprises an aqueous solution containing from about 0.2 to about 20% by weight of a water-soluble electrolyte. The volume to weight ratio of water phase to oil phase is in the range of from about 15:1 to about 125:1.

The monomer component of the oil phase comprises: (i) from about 45 to about 70% by weight of at least one substantially water-insoluble monofunctional monomer capable of forming an atactic amorphous polymer having a Tg of about 35° C. or lower; (ii) from about 10 to about 40% by weight of at least one substantially water-insoluble monofunctional comonomer capable of imparting toughness about equivalent to that provided by styrene; (iii) from about 5 to about 25% by weight of a substantially water-insoluble, polyfunctional crosslinking agent selected from divinyl benzenes, trivinyl benzenes, divinyl toluenes, divinyl xylenes, divinyl naphthalenes divinyl alkylbenzenes, divinyl phenanthrenes, divinyl biphenyls, divinyl diphenylmethanes, divinyl benzyls, divinyl phenylethers, divinyl diphenylsulfides, divinyl furans, divinyl sulfide, divinyl sulfone, polyfunctional acrylates, methacrylates, acrylamides, methacrylamides, and mixtures thereof. The percentages shown as range for crosslinkers and monomers above are expressed on a 100% basis. For example, if a crosslinker is provided as a 50% mixture with another compound, the percentage used in the ranges above refers to 50% of the actual amount of that chemical mixture used.

The emulsion component of the oil phase comprises: (i) a primary emulsifier having at least about 40% by weight emulsifying components selected from diglycerol monoesters of linear unsaturated $C_{16}$–$C_{22}$ fatty acids, diglycerol monoesters of branched $C_{16}$–$C_{24}$ fatty acids, diglycerol monoaliphatic ethers of branched $C_{16}$–$C_{24}$ alcohols, diglycerol monoaliphatic ethers of linear unsaturated $C_{16}$–$C_{22}$ alcohols, diglycerol monoaliphatic ethers of linear saturated $C_{12}$–$C_{14}$ alcohols, sorbitan monoesters of linear unsaturated $C_{16}$–$C_{22}$ fatty acids, sorbitan monoesters of branched $C_{16}$–$C_{24}$ fatty acids, and mixtures thereof; or (ii) the combination a primary emulsifier having at least 20% by weight of these emulsifying components and certain secondary emulsifiers. Preferred secondary emulsifiers are ditallow dimethyl ammonium methyl sulfate and ditallow dimethyl ammonium methyl chloride. When these optional secondary emulsifiers are included in the emulsifier component, it is typically in a weight ratio of primary to secondary emulsifier of from about 50:1 to about 1:4.

The water-in-oil emulsion is preferably formed at a temperature of about 50° C. or higher by mixing the water and oil phases to form a HIPE. For production of HIPEs, the art has typically used mixers that use rotating elements to provide the shear necessary to disperse the internal phase throughout the continuous phase. See, for example, U.S. Pat. No. 5,250,576 (DesMarais, et al.), issued Oct. 5, 1993 and U.S. Pat. No. 5,827,909 (DesMarais), issued Oct. 27, 1998. A process using in-line mixers is described in copending U.S. patent application Ser. No. 09/684,037, entitled "Apparatus and Process for In-Line Preparation of HIPEs", filed in the names of Catalfamo, et al. on Oct. 6, 2000. The individual components used to form the emulsion are described in greater detail below.

B. HIPE Components

1. The Oil Phase

The oil phase of the HIPE can comprise a variety of oily materials. The particular oily materials selected will frequently depend upon the particular use to be made of the HIPE. By "oily" is meant a material, solid or liquid, but preferably liquid at room temperature that broadly meets the following requirements: (1) has very limited solubility in water; (2) has a low surface tension; and (3) possesses a characteristic greasy feel to the touch. Additionally, for those situations where the HIPE is to be used in the food, drug, or cosmetic area, the oily material should be cosmetically and pharmaceutically acceptable. Materials contemplated as oily materials for use in making HIPEs according to the present invention can include, for example, various oily compositions comprising straight, branched and/or cyclic paraffins such as mineral oils, petroleums, isoparaffins, squalanes; vegetable oils, animal oils and marine oils such as tung oil, oiticica oil, castor oil, linseed oil, poppyseed oil, soybean oil, cottonseed oil, corn oil, fish oils, walnut oils, pineseed oils, olive oil, coconut oil, palm oil, canola oil, rapeseed oil, sunflower seed oil, safflower oil sesame seed oil, peanut oil and the like; esters of fatty acids or alcohols such as ethyl hexylpalmitate, $C_{16}$ to $C_{18}$ fatty alcohol di-isootanoates, dibutyl phthalate, diethyl maleate, tricresyl phosphate, acrylate or methacrylate esters, and the like; resin oils and wood distillates including the distillates of turpentine, rosin spirits, pine oil, and acetone oil; various petroleum based products such as gasolines, naphthas, gas fuel, lubricating and heavier oils; coal distillates including benzene, toluene, xylene, solvent naphtha creosote oil and anthracene oil and ethereal oils: and silicone oils. Preferably, the oily material is non-polar.

For preferred HIPEs that are polymerized to form the polymeric foams, this oil phase comprises a monomer component. In the case of HIPE foams suitable for use as absorbents, this monomer component is typically formulated to form a copolymer having a glass transition temperature (Tg) of about 35° C. or lower, and typically from about −10° C. to about 30° C. (The method for determining Tg by Dynamic Mechanical Analysis (DMA) is described in the TEST METHODS section of U.S. Pat. No. 5,650,222, issued to Thomas A. DesMarais, et al. on Jul. 22, 1997, which is incorporated by reference. This monomer component includes: (a) at least one monofunctional monomer whose atactic amorphous polymer has a Tg of about 25° C. or lower; (b) optionally a monofunctional comonomer; and (c) at least one polyfunctional crosslinking agent. Selection of particular types and amounts of monofunctional monomer (s) and comonomer(s) and polyfunctional cross-linking agent(s) can be important to the realization of absorbent HIPE foams having the desired combination of structure, mechanical, and fluid handling properties that render such materials suitable for use as absorbents for aqueous fluids.

For HIPE foams useful as absorbents, the monomer component comprises one or more monomers that tend to impart rubber-like properties to the resulting polymeric foam structure. Such monomers can produce high molecular weight (greater than 10,000) atactic amorphous polymers having Tgs of about 25° C. or lower. Monomers of this type include, for example, monoenes such as the ($C_4$–$C_{14}$) alkyl acrylates such as butyl acrylate, hexyl acrylate, octyl acrylate, 2-ethylhexyl acrylate, nonyl acrylate, decyl acrylate, dodecyl (lauryl) acrylate, isodecyl acrylate tetradecyl acrylate, aryl acrylates and alkaryl acrylates such as benzyl acrylate, nonylphenyl acrylate, the ($C_6$–$C_{16}$) alkyl methacrylates such as hexyl acrylate, octyl methacrylate, nonyl methacrylate, decyl methacrylate, isodecyl methacrylate, dodecyl (lauryl) methacrylate, tetradecyl methacrylate, ($C_4$–$C_{12}$) alkyl styrenes such as p-n-octylstyrene, acrylamides such as N-octadecyl acrylamide, and polyenes such as 2-methyl-1,3-butadiene (isoprene), butadiene, 1,3-pentadiene (piperylene), 1,3-hexadiene, 1,3-heptadiene, 1,3-octadiene, 1,3-nonadiene, 1,3-decadiene, 1,3-undecadiene, 1,3-dodecadiene, 2-methyl-1,3-hexadiene, 6-methyl-1,3-heptadiene, 7-methyl-1,3-octadiene, 1,3,7-octatriene, 1,3,9-decatriene, 1,3,6-octatriene, 2,3-dimethyl-1,3-butadiene, 2-methyl-3-ethyl-1,3-butadiene, 2-methyl-3-propyl-1,3-butadiene, 2-amyl-1,3-butadiene, 2-methyl-1,3-pentadiene, 2,3-dimethyl-1,3-pentadiene, 2-methyl-3-ethyl-1,3-pentadiene, 2-methyl-3-propyl-1,3-pentadiene, 2,6-diethyl-1,3,7-octatriene, 2,7-dimethyl-1,3,7-octatriene, 2,6-dimethyl-1,3,6-octatriene, 2,7-dimethyl-1,3,6-octatriene, 7-methyl-3-methylene-1,6-octadiene (myrcene), 2,6-dimethyl-1,5,7-octatriene (ocimene), 1-methyl-2-vinyl4,6-hepta-dieny-3,8-nonadienoate, 5-methyl-1,3,6-heptatriene, 2-ethylbutadiene, and mixtures of these monomers. Of these monomers, isodecyl acrylate, n-dodecyl acrylate and 2-ethylhexyl acrylate are the most preferred. The monomer will generally comprise 30 to about 85%, more preferably from about 50 to about 70%, by weight of the monomer component.

For HIPE foams useful as absorbents, the monomer component also typically comprises one or more comonomers that are typically included to modify the Tg properties of the resulting polymeric foam structure, its modulus (strength), and its toughness. These monofunctional comonomer types can include styrene-based comonomers (e.g., styrene and ethyl styrene) or other monomer types such as methyl methacrylate where the related homopolymer is well known as exemplifying toughness. Another example of a monomer which confers a high level of toughness to the resulting HIPE foam is isoprene and related dienes such as piperylene and dimethylbutadiene. Of these comonomers, styrene, ethyl styrene, and mixtures thereof are particularly preferred for imparting toughness to the resulting polymeric foam structure. These comonomers can comprise up to about 40% of the monomer component and will normally comprise from about 5 to about 40%, preferably from about 10 to about 35%, most preferably from about 15 about 30%, by weight of the monomer component.

For HIPE foams useful as absorbents, this monomer component also includes one or more polyfunctional crosslinking agents. The inclusion of these crosslinking agents tends to increase the Tg of the resultant polymeric foam as well as its strength with a resultant loss of flexibility and resilience. Suitable crosslinking agents include any of those that can be employed in crosslinking rubbery diene monomers, such as divinylbenzenes, divinyltoluenes, divinylxylenes, divinylnaphthalenes divinylalkylbenzenes, divinylphenanthrenes, trivinylbenzenes, divinylbiphenyls, divinyldiphenylmethanes, divinylbenzyls, divinylphenylethers, divinyldiphenylsulfides, divinylfurans, divinylsulfone, divinylsulfide, divinyldimethylsilane, 1,1'-divinylferrocene, 2-vinylbutadiene, maleate, di-, tri-, tetra-, penta- or higher (meth)acrylates and di-, tri-, tetra-, penta- or higher (meth)acrylamides, including ethylene glycol dimethacrylate, neopentyl glycol dimethacrylate, 1,3-butanediol dimethacrylate, 1,4-butanediol dimethacrylate, 1,6-hexanediol dimethacrylate, 2-butenediol dimethacrylate, diethylene glycol dimethacrylate, hydroquinone dimethacrylate, catechol dimethacrylate, resorcinol dimethacrylate, triethylene glycol dimethacrylate, polyethylene glycol dimethacrylate; trimethylolpropane trimethacrylate, pentaerythritol tetramethacrylate, 1,3-butanediol diacrylate, 1,4-butanediol diacrylate, 1,6-hexanediol diacrylate, diethylene glycol diacrylate, hydroquinone diacrylate, catechol diacrylate, resorcinol diacrylate, triethylene glycol diacrylate, polyethylene glycol diacrylate; pentaerythritol tetraacrylate, 2-butenediol diacrylate, tetramethylene diacrylate, trimethyol propane triacrylate, pentaerythritol tetraacrylate, N-methylolacrylamide, 1,2-ethylene bisacrylamide, 1,4-butane bisacrylamide, and mixtures thereof.

The preferred polyfunctional crosslinking agents include divinylbenzene, ethylene glycol dimethacrylate, diethylene glycol dimethacrylate, 1,6-hexanediol dimethacrylate, 2-butenediol dimethacrylate, ethylene glycol diacrylate, diethylene glycol diacrylate, 1,6-hexanediol diacrylate, 2-butenediol diacrylate, trimethylolpropane triacrylate and trimethacrylate, and mixtures thereof. Divinyl benzene is typically available as a mixture with ethyl styrene in proportions of about 55:45. These proportions can be modified so as to enrich the oil phase with one or the other component. It can be advantageous to enrich the mixture with the ethyl styrene component while simultaneously omitting inclusion of styrene from the monomer blend. The preferred ratio of divinyl benzene to ethyl styrene is from about 30:70 to 55:45, most preferably from about 35:65 to about 45:55. The inclusion of higher levels of ethyl styrene imparts the required toughness without increasing the Tg of the resulting copolymer to the degree that styrene does. The cross-linking agent can generally be included in the oil phase of the HIPE in an amount of from about 3 to about 40%, more preferably from about 4 to about 40%, most preferably from about 5 to about 40%, by weight of the monomer component (100% basis).

The major portion of the oil phase of these preferred HIPEs will comprise these monomers, comonomers and crosslinking agents. It is essential that these monomers, comonomers and crosslinking agents be substantially water-insoluble so that they are primarily soluble in the oil phase and not the water phase. Use of such substantially water-insoluble monomers ensures that HIPE of appropriate characteristics and stability will be realized.

It is, of course, highly preferred that the monomers, comonomers and crosslinking agents used herein be of the type such that the resulting polymeric foam is suitably non-toxic and appropriately chemically stable. These monomers, comonomers and cross-linking agents should preferably have little or no toxicity if present at very low residual concentrations during post-polymerization foam processing and/or use.

2. Emulsifier Component

Another typical component of the oil phase is an emulsifier (or emulsifiers) that permits the formation of stable HIPE emulsions. Suitable emulsifiers for use herein can include any of a number of conventional emulsifiers applicable for use in low and mid-internal-phase emulsions. The particular emulsifiers used will depend upon an number of factors, including the particular oily materials present in the oil phase and the particular use to be made of the HIPE. Usually, these emulsifiers are nonionic materials and can have a wide range of HLB values. Examples of some typical emulsifiers include sorbitan esters such as sorbitan laurates (e.g., SPAN® 20), sorbitan palmitates (e.g., SPAN® 40), sorbitan stearates (e.g., SPAN® 60 and SPAN® 65), sorbitan monooleates (e.g., SPAN® 80), sorbitan trioleates (e.g., SPAN® 85), sorbitan sesquioleates (e.g., EMSORB® 2502), and sorbitan isostearates (e.g., CRILL® 6); polyglycerol esters and ethers (e.g., TRIODAN® 20); polyoxyethylene fatty acids, esters and ethers such as polyoxyethylene (2) oleyl ethers, polyethoxylated oleyl alcohols (e.g., BRIJ® 92 and SIMUSOL® 92), etc.; mono-, di-, and triphosphoric esters such as mono-, di-, and triphosphoric esters of oleic acid (e.g., HOSTAPHAT), polyoxyethylene sorbitol esters such as polyoxyethylene sorbitol hexastearates (e.g., ATLAS® G-1050), ethylene glycol fatty acid esters, glycerol mono-isostearates (e.g., IMWITOR 780K), ethers of glycerol and fatty alcohols (e.g., CREMOPHOR WO/A), esters of polyalcohols, synthetic primary alcohol ethylene oxide condensates (e.g., SYNPERONIC A2), mono and diglycerides of fatty acids (e.g., ATMOS® 300), and the like.

Other preferred emulsifiers include the diglycerol esters derived from monooleate, monomyristate, monopalmitate, and monoisostearate acids. A preferred coemulsifier is ditallowdimethyl ammonium methyl sulfate. Mixtures of these emulsifiers are also particularly useful, as are purified versions of each, specifically sorbitan esters containing minimal levels of isosorbide and polyol impurities.

For preferred HIPEs that are polymerized to make polymeric foams, the emulsifier can serve other functions besides stabilizing the HIPE. These include the ability to hydrophilize the resulting polymeric foam. The resulting polymeric foam is typically washed and dewatered to remove most of the water and other residual components. This residual emulsifier can, if sufficiently hydrophilic, render the otherwise hydrophobic foam sufficiently wettable so as to be able to absorb aqueous fluids.

For preferred HIPEs that are polymerized to make polymeric foams, suitable emulsifiers can include sorbitan monoesters of branched $C_6$–$C_{24}$ fatty acids, linear unsaturated $C_{16}$–$C_{22}$ fatty acids, and linear saturated $C_{12}$–$C_{14}$ fatty acids, such as sorbitan monooleate, sorbitan monomyristate, and sorbitan monoesters derived from coconut fatty acids; diglycerol monoesters of branched $C_{16}$–$C_{24}$ fatty acids, linear unsaturated $C_{16}$–$C_{22}$ fatty acids, or linear saturated $C_{12}$–$C_{14}$ fatty acids, such as diglycerol monooleate (i.e., diglycerol monoesters of C18:1 fatty acids), diglycerol monomyristate, diglycerol monoisostearate, and diglycerol monoesters of coconut fatty acids; diglycerol monoaliphatic ethers of branched $C_{16}$–$C_{24}$ alcohols (e.g., Guerbet alcohols), linear unsaturated $C_{16}$–$C_{22}$ alcohols, and linear saturated $C_{12}$–$C_{14}$ alcohols (e.g., coconut fatty alcohols), and mixtures of these emulsifiers. See U.S. Pat. No. 5,287,207 (Dyer et al.), issued Feb. 7, 1995 (herein incorporated by reference) which describes the composition and preparation suitable polyglycerol ester emulsifiers and U.S. Pat. No. 5,500,451, issued Mar. 19, 1996 to Stephen A. Goldman et al. (which is incorporated by reference herein), which describes the composition and preparation suitable polyglycerol ether emulsifiers. Preferred emulsifiers include sorbitan monolaurate (e.g., SPAN® 20, preferably greater than about 40%, more preferably greater than about 50%, most preferably greater than about 70% sorbitan monolaurate), sorbitan monooleate (e.g., SPAN® 80, preferably greater than about 40%, more preferably greater than about 50%, most preferably greater than about 70% sorbitan monooleate), diglycerol monooleate (e.g., preferably greater than about 40%, more preferably greater than about 50%, most preferably greater than about 70% diglycerol monooleate), diglycerol monoisostearate (e.g., preferably greater than about 40%, more preferably greater than about 50%, most preferably greater than about 70% diglycerol monoisostearate), diglycerol monomyristate (e.g., preferably greater than about 40%, more preferably greater than about 50%, most preferably greater than about 70% sorbitan monomyristate), the cocoyl (e.g., lauryl and myristoyl) ethers of diglycerol, and mixtures thereof.

In addition to these primary emulsifiers, co-emulsifiers can be optionally included in the oil phase. These co-emulsifiers are at least cosoluble with the primary emulsifier in the oil phase. Suitable co-emulsifiers can be zwitterionic types, including the phosphatidyl cholines and phosphatidyl choline-containing compositions such as the lecithins and aliphatic betaines such as lauryl betaine; cationic types, including long chain $C_{12}$–$C_{22}$ dialiphatic, short chain $C_1$–$C_4$ dialiphatic quaternary ammonium salts such as ditallow dimethyl ammonium chloride, bistridecyl dimethyl ammonium chloride, and ditallow dimethyl ammonium methylsulfate, the long chain $C_{12}$–$C_{22}$ dialkoyl(alkenoyl)-2-hydroxyethyl, short chain $C_1$–$C_4$ dialiphatic quaternary ammonium salts such as ditallowoyl-2-hydroxyethyl dimethyl ammonium chloride, the long chain $C_{12}$–$C_{22}$ dialiphatic imidazolinium quaternary ammonium salts such as methyl-1-tallow amido ethyl-2 -tallow imidazolinium methylsulfate and methyl-1-oleyl amido ethyl-2-oleyl imidazolinium methylsulfate, the short chain $C_1$–$C_4$ dialiphatic, long chain $C_{12}$–$C_{22}$ monoaliphatic benzyl quaternary ammonium salts such as dimethyl stearyl benzyl ammonium chloride and dimethyl tallow benzyl ammonium chloride, the long chain $C_{12}$–$C_{22}$ dialkoyl(alkenoyl)-2-aminoethyl, short chain $C_1$–$C_4$ monoaliphatic, short chain $C_1$–$C_4$ monohydroxyaliphatic quaternary ammonium salts such as ditallowoyl-2-aminoethyl methyl 2-hydroxypropyl ammonium methyl sulfate and dioleoyl-2-aminoethyl methyl 2-hydroxyethyl ammonium methyl sulfate; anionic types including the dialiphatic esters of sodium sulfosuccinic acid such as the dioctyl ester of sodium sulfosuccinic acid and the bistridecyl ester of sodium sulfosuccinic acid, the amine salts of dodecylbenzene sulfonic acid; and mixtures of these secondary emulsifiers. The preferred secondary emulsifiers are ditallow dimethyl ammonium methyl sulfate and ditallow dimethyl ammonium methyl chloride. When these optional secondary emulsifiers are included in the emulsifier component, it is typically at a weight ratio of primary to secondary emulsifier of from about 50:1 to about 1:4, preferably from about 30:1 to about 2:1.

3. Oil Phase Composition

The oil phase used to form the HIPE according to the process of the present invention can comprise varying ratios of oily materials and emulsifier. The particular ratios selected will depend on a number of factors including the oily materials involved, the emulsifier used, and the use to be made of the HIPE. Generally, the oil phase can comprise from about 50 to about 98% by weight oily materials and from about 2 to about 50% by weight emulsifier. Typically, the oil phase will comprise from about 70 to about 97% by weight of the oily materials and from about 3 to about 30% by weight emulsifier, and more typically from about 85 to about 97% by weight of the oily materials and from about 3 to about 15% by weight emulsifier. For preferred HIPEs used to make polymeric foams, the oil phase will generally comprise from about 65 to about 98% by weight monomer component and from about 2 to about 30% by weight emulsifier component. Preferably, the oil phase will comprise from about 80 to about 97% by weight monomer component and from about 3 to about 20% by weight emulsifier component. More preferably, the oil phase will comprise from about 90 to about 97% by weight monomer component and from about 3 to about 10% by weight emulsifier component.

In addition to the monomer and emulsifier components, the oil phase of these preferred HIPEs can contain other optional components. One such optional component is an oil soluble polymerization initiator of the general type well known to those skilled in the art, such as described in U.S. Pat. No. 5,290,820 (Bass et al.), issued Mar. 1, 1994, which is incorporated by reference. Another possible optional component is a substantially water insoluble solvent for the monomer and emulsifier components. Use of such a solvent is not preferred, but if employed will generally comprise no more than about 10% by weight of the oil phase.

A preferred optional component is an antioxidant such as a Hindered Amine Light Stabilizer (HALS), such as bis-1,2,2,5,5-pentamethylpiperidinyl) sebacate (Tinuvin 765) or a Hindered Phenolic Stabilizer (HPS) such as Irganox 1076 and t-butylhydroxyquinone. Another preferred optional component is a plasticizer such as dioctyl azelate, dioctyl sebacate or dioctyl adipate. Other optional components include fillers, colorants, fluorescent agents, opacifying agents, chain transfer agents, and the like.

C. Water Phase Components

The internal water phase of the HIPE is generally an aqueous solution containing one or more dissolved components. One dissolved component of the water phase is a water-soluble electrolyte. The dissolved electrolyte minimizes the tendency of the components in the oil phase to also dissolve in the water phase. For preferred HIPEs used to make polymeric foams, this is believed to minimize the extent to which polymeric material fills the cell windows at the oil/water interfaces formed by the water phase droplets during polymerization. Thus, the presence of electrolyte and the resulting ionic strength of the water phase is believed to determine whether and to what degree the resulting preferred HIPE foams can be open-celled.

Any electrolyte capable of imparting ionic strength to the water phase can be used. Preferred electrolytes are mono-, di-, or trivalent inorganic salts such as the water-soluble halides, e.g., chlorides, nitrates and sulfates of alkali metals and alkaline earth metals. Examples include sodium chloride, calcium chloride, sodium sulfate and magnesium sulfate. For HIPEs that are used to make polymeric foams, calcium chloride has been found to be suitable for use in the process according to the present invention. Generally the electrolyte will be utilized in the water phase of the HIPE in a concentration in the range of from about 0.2 to about 30% by weight of the water phase. More preferably, the electrolyte will comprise from about 1 to about 20% by weight of the water phase.

For HIPEs used to make polymeric foams, a polymerization initiator is typically included in the HIPE. Such an initiator component can be added to the water phase of the HIPE and can be any conventional water-soluble free radical initiator. These include peroxygen compounds such as sodium, potassium and ammonium persulfates, hydrogen peroxide, sodium peracetate, sodium percarbonate and the like. Conventional redox initiator systems can also be used. Such systems are formed by combining the foregoing peroxygen compounds with reducing agents such as sodium bisulfite, L-ascorbic acid or ferrous salts. The initiator can be present at up to about 20 mole percent based on the total moles of polymerizable monomers in the oil phase. Preferably, the initiator is present in an amount of from about 0.001 to 10 mole percent based on the total moles of polymerizable monomers in the oil phase.

Molding

Once formed, the HIPE is deposited into a mold where it will be subsequently cured (polymerized and crosslinked). In the simplest embodiment, the mold can comprise a cylindrical tub or other simple geometric shape constructed of polyethylene or other material compatible with the HIPE from which the eventually cured solid foam material can be easily removed for further processing (e.g. spiral cutting into a continuous web as described in U.S. patent application Ser. No. 09/255,126, filed in the name of DesMarais, et al. on Feb. 22, 1999) after curing has been carried out to the extent desired. However, it will be readily recognized that there are many opportunities for improving such a simple batch molding process. In particular, simple geometric shapes fail to provide individual components having a complex tridimensional structure, such as the absorbent cores 24 discussed above. Similarly, such simple molding processes do not have the advantages of a continuous or semi-continuous molding process that can be used to provide tridimensional implements such as those discussed above.

Molds for use in the present invention can be prepared using methods known to the art for such purposes. For example a master defining the intended shape to be molded can be prepared using sculpting techniques. The individual mold components can then be formed around the master using a technique such as vacuum forming. Alternatively techniques, such as lost wax casting, direct machining, electrical discharge machining, and other means as are known to the art can also be used to prepare molds for processes intended for higher production rates where a molding method similar to injection molding can be used (see discussion of the process below).

A mold for purposes of the present invention must be compatible with the HIPE that is deposited therein and with the curing process. In particular, contact of the HIPE with the mold material should not cause the HIPE to "break" (i.e., separate into the constituent oil and water phases). The mold material must also be compatible with the environmental conditions during the curing step. Specifically, the material used to fabricate a mold must maintain satisfactory dimensional stability when exposed to the temperatures and internal pressures of the curing process. For curing at atmospheric pressure (i.e., the curing temperature is between about 50° C. and about 100° C.) molds made of polyester, polypropylene, and polyethylene naphthalate have been found to be suitable. Preferred are the 2,6 dimethylnaphthalate resins as are available from Shell Chemical Company of Houston, Tex. as HIPERTUF. For pressurized curing processes (i.e., curing at greater than about 100° C.) metallic molds are desired because of their superior durability. Glass or glass-lined molds are also suitable.

If desired, the mold can be lined with a mold release agent as may be known to the art. It is particularly preferred to use the same material that is used as the primary emulsifier (see discussion above) as a mold release agent because such use enhances the stability of the HIPE at the HIPE/mold interface. The mold release agent may be applied to the mold surface using any convenient means, such as wiping, spraying (e.g., from the melt), solution application (it is important to insure the solvent is completely evaporated before filling the mold), and the like.

Figure 5:
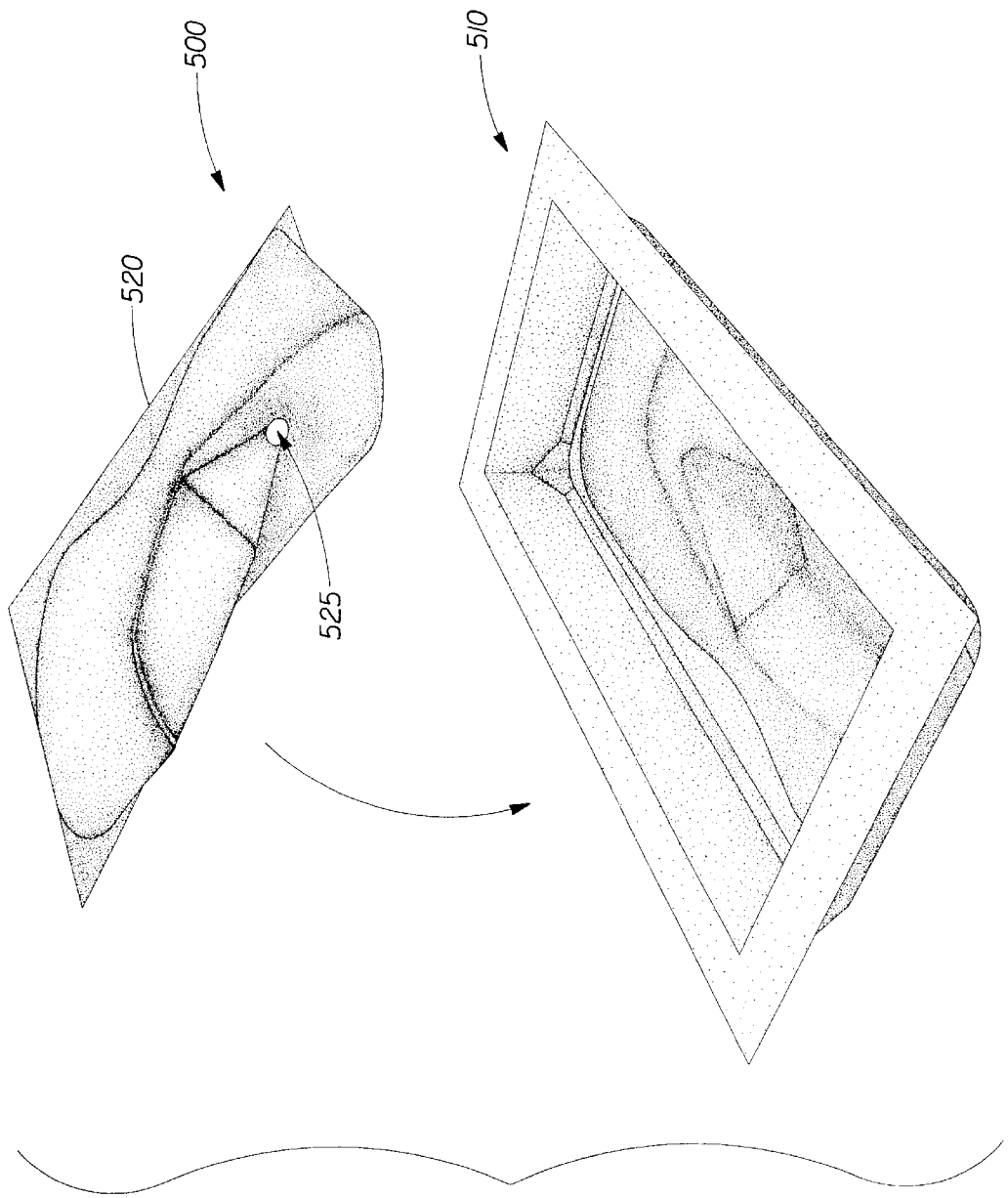
FIG. 5 is an exploded perspective view of a mold for forming a tridimensional HIPE foam according to the method of the present invention.

As noted above the formed HIPE is deposited into a mold for subsequent curing. This deposition step can be as simple as pouring the HIPE into a cavity that has been provided with a predetermined tridimensional configuration so one surface of the resulting HIPE foam has the desired shape and the other surface is substantially flat. FIG. 5 shows a mold 500 that is useful in a variation of this process that can be used to produce implements having tridimensionality on both the top and bottom surfaces. In this process, a slight excess of the HIPE is poured into a female cavity 510 and a male mold part 520, having one or more vent(s) 525, is inserted into the mold 500. Entrained air and a small portion of the HIPE pass through the vent(s) 525 as the mold parts 510, 520 are mated. Such a molding process is particularly useful in producing prototype molded articles from HIPE foams because the male and female mold parts 510, 520 can be vacuum formed around a master part design from a compatible material such as polyester or poly vinylnapthalene using very simple processes and the HIPE can be cured in the molds at atmospheric pressures.

For commercial production, higher speed processes are desirable. A simple embodiment (not shown) of a higher speed process involves providing a sequence of mold cavities similar to female cavity 510 or other desired tridimensional shape (e.g., on a belt) and pouring the HIPE into the individual cavities, curing the HIPE in the cavities, and stripping the cured HIPE foam therefrom so as to continuously produce molded HIPE foam implements that are tridimensional on one side and relatively flat on the other side.

In another embodiment the process (also not shown) of the present invention comprises a process substantially like injection molding (See the discussion beginning on page 8–45 of Hanlon, Joseph F. ed., *Handbook of Package Engineering*, McGraw-Hill, New York, 1971 for an overview of injection molding.) can be used. In such a process, the HIPE is injected into a plurality of mold cavities through runners. Venting is provided along the part line between the mold sections and the mold cavities are oriented to insure that each cavity is completely filled by each shot. The mold can also be provided with heating means to provide the needed energy to cure the HIPE. Alternatively, the filled mold can be heated using external means to provide the cure energy. As will be recognized such a process is semi-continuous in that individual mold cavities are filled while the HIPE formation process continues to operate continuously.

Figure 6:
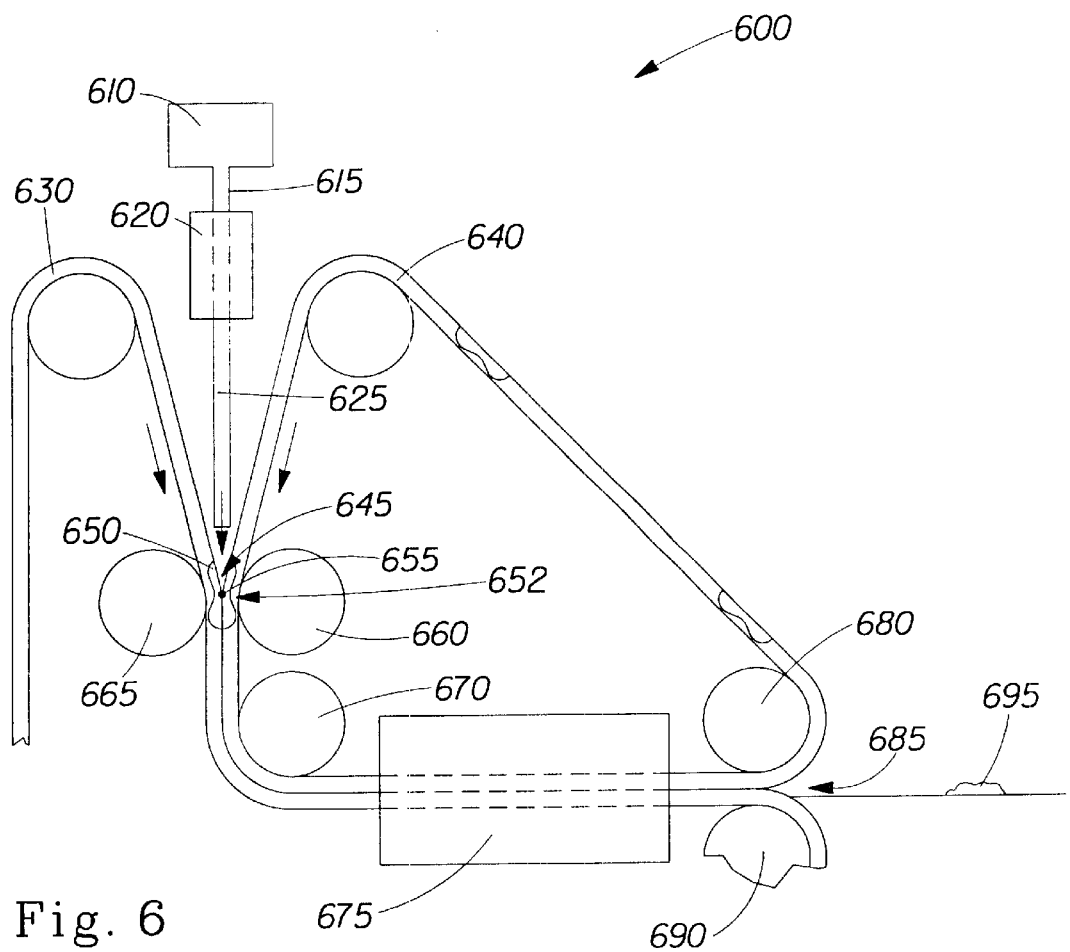
FIGS. 6–8 are diagrammatic views of various molding processes according to the present invention.
Figure 7:
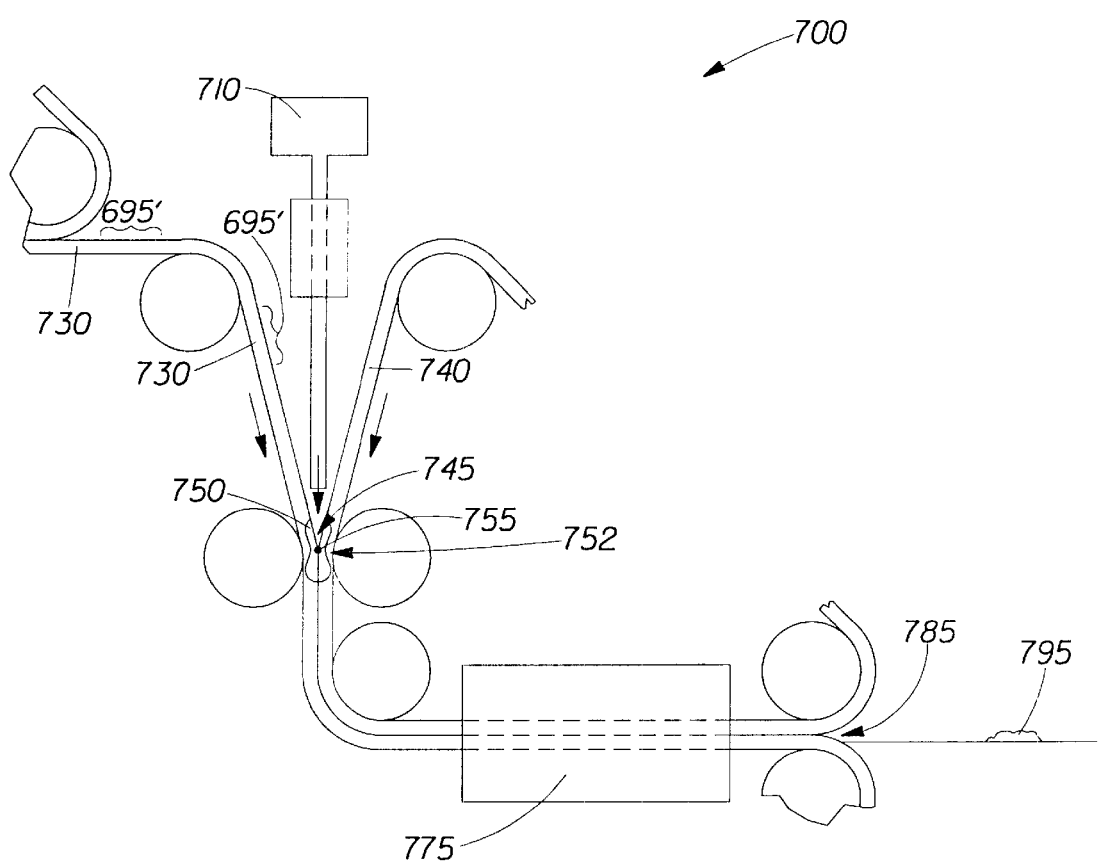
Figure 8:
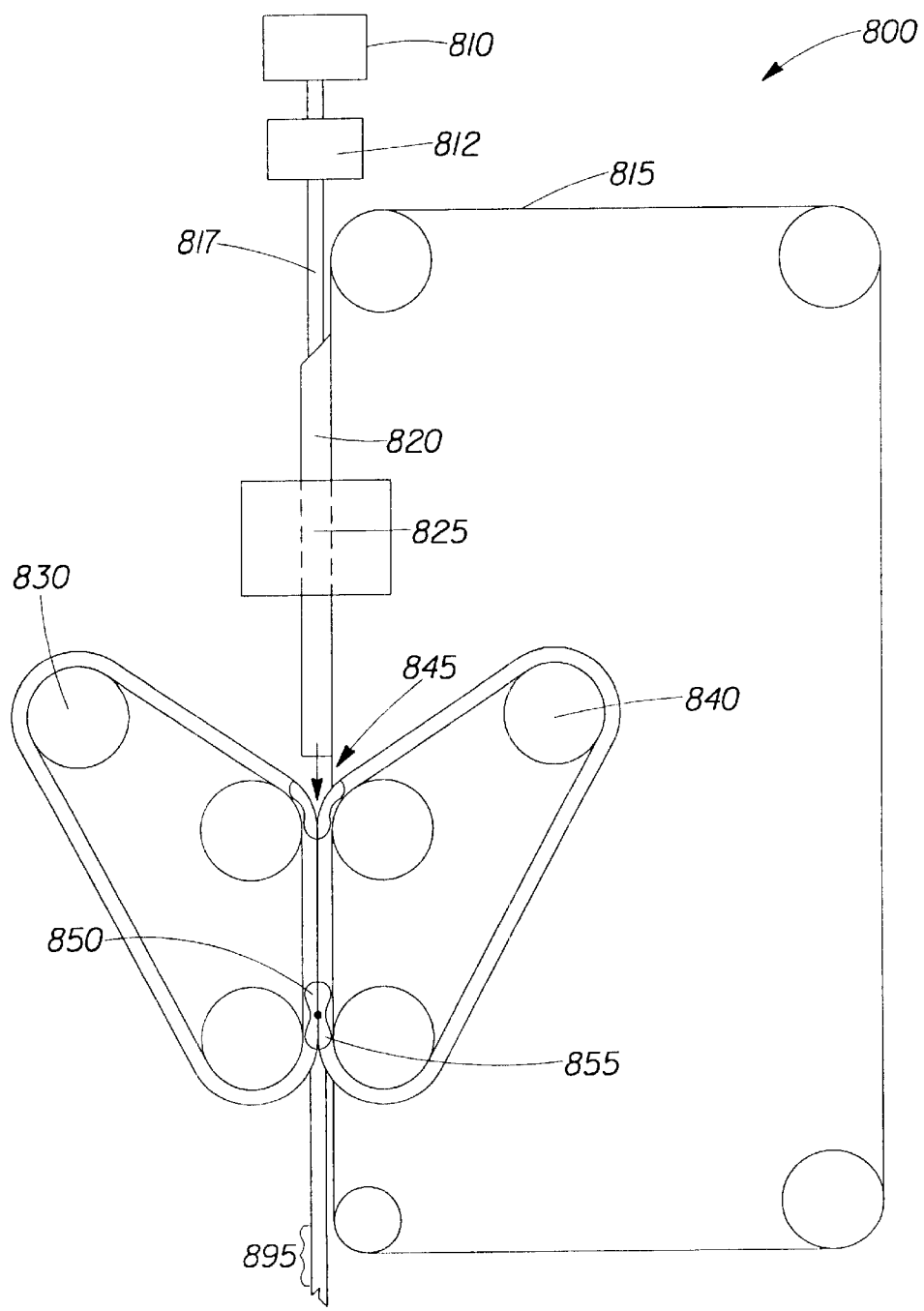

FIGS. 6–8 show unit operations for a continuous molding process for forming tridimensional HIPE foams. As used herein, a "continuous process" is one wherein the cycle time for filling an individual mold is sufficiently short so that the HIPE does not enter the gel phase while the mold is being filled. In general the processes shown in FIGS. 6–8 comprises forming a mold cavity from a plurality of cavity portions (Shown as mold cavity halves in FIGS. 6–8). Before the portions are fully closed the mold cavity is filled with a HIPE which is cured into a HIPE foam in the mold cavity. The HIPE foam is then stripped from the mold cavity as a molded, tridimensional HIPE foam implement.

FIG. 6 shows a portion of a process 600 where individual mold cavity halves 650, 655 are a pair of a plurality of such pairs carried on a pair of continuous belts 630, 640. In the process of FIG. 6, the finished HIPE is provided by HIPE preparation system 610 using one of the methods discussed above and carried therefrom by supply pipe 615. The HIPE passes through an optional preheater 620 which can be used to further increase the HIPE temperature from an emulsification temperature to a desired curing temperature (as will be discussed below, it is important to insure that the HIPE is deposited into the mold before curing reaches the "gel point" stage). The HIPE is then deposited into the mold cavity 645 by delivery means 625. Delivery means 625 is designed so as to provide the requisite quantity of the HIPE to fill mold cavity 645 with little or no excess. For example delivery means 625 could comprise a nozzle/shutoff valve combination (not shown) for control of HIPE flow. If desired a recycle loop or accumulator (neither element shown) could be used to manage flow when there is no HIPE delivery to mold cavity 645. Alternatively, designs having a lateral stagger between the pairs of mold halves 650, 655 combined with paired delivery nozzles and a flow diverter (not shown) could be used so as to maintain a substantially continuous flow of HIPE to molding process 600.

As can be seen in FIG. 6, at least a portion of the cavity halves 650, 655 have been brought together by nip rolls 660, 665 so mold cavity 645 is open only above convergence point 652. As mold cavity 645 progresses between nip rolls 660, 665, it is filled with the HIPE and ultimately is completely closed (i.e., convergence point 652 passes beyond the trailing end of cavity 645). Such a method provides for filling cavity 645 with minimal air entrapment and wasted HIPE because the flow rate and flow cutoff can be programmed so as to substantially fill cavity 645 immediately before convergence point 652 passes through the nip rolls 660, 665.

The mated cavity halves 650, 655 pass turning roll 670 which serves to maintain the combining force holding the belts 630, 640 together. As will be recognized, it is necessary to maintain a combining force to hold belts 630, 640 in a closed configuration until the HIPE is cured past the gel point (see discussion below). If belt tension is insufficient, means (not shown) can be provided to hold belt edges together. Mold cavity 645, with the entrained HIPE then passes through curing region 675 where the HIPE is substantially cured into a HIPE foam. Curing region 675 may be heated as necessary to maintain the HIPE at a curing temperature. After curing is completed, the cavity 645 passes from curing region 675 and a pair of turning rolls 680, 690 causes belts 630, 640 to diverge at divergence point 685. The molded, tridimensional article 695 is then stripped from cavity 645 and taken away.

Figure 6A:
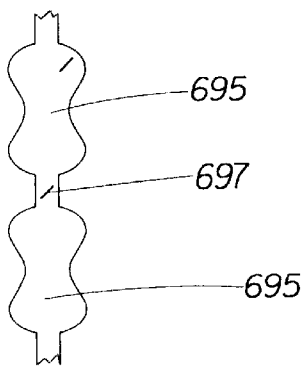
FIG. 6A illustrates a continuous web of individual articles connected by a small isthmus.

The process of the present invention is amenable to several variations. In one such variation, shown in FIG. 6A, consecutive mold cavities are connected by a channel (not shown) so as to create a continuous web of individual articles 695 that are connected by a small isthmus 697. Such webs have the advantage in that they are more readily manipulated in subsequent converting operations. For example, such a web can be festooned for delivery to a converting operation wherein the web provides cores 24 when the isthmus is cut to separate individual articles 695 (i.e., cores 24) that can then be provided with a topsheet 22 and a backsheet 23 to form a sanitary napkin similar to sanitary napkin 20 described above.

In another alternative embodiment, shown in FIG. 7, two HIPEs having different properties can be combined into a single molded article. After the belts diverge at divergence point 685, the molded article 695' would only partially fill lower mold cavity half 650 and remains therein. Upper mold cavity half 655 can be designed so as to enhance connectivity between the two HIPEs. The partially finished article 695' then enters a second molding station 700 where the steps described above are substantially repeated. Specifically, belts 730 (a continuation of belt 630) with lower mold cavity half 750 is mated with belt 740 having with mold cavity half 755 at convergence point 752 to form mold cavity 745 which is filled by a second HIPE from HIPE preparation system 710. The mold cavity 745 then progresses through second curing region 775 where the second HIPE is cured, the belts are separated at divergence point 785 and a finished molded tridimensional article comprising two different HIPEs 795 is stripped from cavity 745. Such cavities could also be connected by a channel to form a continuous web as described above.

In another alternative embodiment, shown as 800 in FIG. 8, an impermeable membrane can be interposed between one or both of belts 830 and 840. Such a membrane could allow the use of less compatible but more durable materials for belts 830 and 840. The membrane can take several forms. In all of the forms the membrane conforms to the shape of the cavity halves allowing the cured HIPE to conform thereto also. In one embodiment (not shown), the membrane could comprise a material that becomes joined to the molded article and ultimately becomes a part of a finished product made using the molded article (e.g., a backsheet for an absorbent article). In another embodiment (also not shown) the membrane is a disposable material that aids in the formation of the finished molded article (i.e., the membrane is unwound upstream of the molding process and separated from the molded HIPE foam article for ultimate disposal after a single use). In the embodiment shown in FIG. 8, the membrane 815 is a reusable material that releasably contains the HIPE during the molding and curing processes.

As shown in FIG. 8 HIPE is provided by HIPE preparation system 810. Membrane 815 is preformed using formation means 820 into a configuration capable of containing the HIPE (e.g., by forming into a trough or other partially closed configuration). The optionally preheated HIPE (via first heating means 812) is delivered by delivery means 817 to the preformed membrane 815. If desired, the HIPE can optionally be further heated to a cure temperature by second heating means 825. The HIPE-filled membrane 815 then contacts belts 830 and 840 which have a plurality of mold cavity halves 850, 855 disposed thereon. Means, such as vacuum or hydrostatic pressure maybe used to cause membrane 815 and the HIPE contained therein to conform to the shaped mold cavities 850, 855. The belts 830, 840 converge in a manner similar to that shown in FIGS. 5 and 6 so that mold cavity halves 850, 855 become mated forming a HIPE-filled mold cavity 845. The mated cavity halves are maintained at a temperature sufficient to cure the HIPE for sufficient time for curing to be substantially completed and are then separated releasing membrane 815 and the cured RIPE from mold cavity halves 850, 855. The molded HIPE foam implement 895 is stripped from membrane 815 and membrane 815 is optionally cleaned before being cycled back (e.g., by a series of turning rolls (not shown)) for another molding sequence.

Optional Mold-Related Process Steps

The molding process of the present invention is also amenable to several optional process steps that can be used to optimize production of the HIPE foams produced thereby. Exemplary steps of this type are discussed in the following paragraphs.

Preheated Mold Cavities

In one desirable yet optional process step, the mold cavities where the HIPE foam is formed by curing a HIPE deposited therein can be preheated to approximately the desired curing temperature. Such preheating is advantageous because it minimizes/eliminates any thermal shock that the HIPE may experience as the mold is filled. Such shock can, for example, cause the HIPE to break at the interface between the HIPE and the surrounding mold resulting in the formation of a "skin" surrounding the molded implement. As will be recognized, such a "skin" is very undesirable if the implement is to be used as an absorbent structure.

Precuring

In some instances, it may be desirable to precure the HIPE (i.e., maintain the HIPE at a curing temperature for a short period of time before depositing it into a mold). Such precuring has the advantage of shortening the residence time in the mold before the finished molded HIPE foam implement is removed therefrom. Precuring may also be advantageous in situations where the implement is molded in two portions as described above so as to minimize/prevent migration of HIPE components from the second portion into the already cured first portion.

Postcuring

Postcuring may also be desirable in some instances. As used herein, "postcuring" describes a process wherein a molded, partially cured HIPE is removed from the mold with curing being completed in a subsequent process step. As will be recognized, a process comprising a postcuring step will make particularly efficient use of mold cavities. Also, it should be noted that curing must be sufficiently advanced so that the partially cured implement has sufficient mechanical integrity to maintain its molded shape after being removed from the mold cavity.

Curing

The monomer component is then polymerized and crosslinked (i.e., cured) in the mold, as briefly discussed above, to form the HIPE foam material. It is usually preferred that the temperature at which the HIPE is deposited into the mold be approximately the same as the curing temperature.

Suitable curing conditions will vary depending upon the monomer and other components of the oil and water phases of the emulsion (especially the emulsifier systems used), and the type and amounts of polymerization initiators used. In brief, the temperature needs to be sufficient for sufficient free radicals to be generated by decomposition of the initiator to initiate the polymerization and crosslinking reactions. Frequently, however, suitable curing conditions will involve maintaining the HIPE at elevated temperatures above about 50°0 C. for about 18 hours. Curing can be accelerated by exposure to higher temperatures and, if necessary, containment under super atmospheric pressures so the aqueous continuous phase does not evaporate. Such increased temperature curing is described in copending U.S. patent application Ser. No. 09/255,225, filed in the name of DesMarais, et al. on Feb. 22, 1999.

In some cases it may be desirable to form the HIPE at an emulsification temperature and subsequently heat the HIPE to a curing temperature. In such instances, it is necessary that the time between HIPE formation and deposition into the molds not be so long that the HIPE has already begun to cure such that it reaches the gel point. As used herein the term "gel point" is intended to describe that state of a partially cured HIPE wherein the polymerization has progressed to the point that the HIPE substantially comprises partially formed polymer whereby it cannot be disturbed by further process steps (e.g., molding) without diminishing the physical properties of the ultimately cured polymer. Without being bound by theory, it is believed that the gel point is reached when the polymerization has substantially consumed all of the monomer into predominately linear polymeric molecules and the crosslinking step that joins the predominately linear molecules to form the cured HIPE commences.

Post Curing Processing

A porous water-filled open-celled HIPE foam is typically obtained after curing in the molds of the present invention. The solid polymerized HIPE foam will generally be filled with residual water phase material used to prepare the HIPE. This residual water phase material (generally an aqueous solution of electrolyte, residual emulsifier, and polymerization initiator) should be at least partially removed prior to further processing and use of the foam. The foam may be dewatered by compressing the foam structure to squeeze out residual liquid and/or by washing the foam structure with water or other aqueous washing solutions. Frequently several compressing and washing steps, e.g., from 2 to 4 cycles, will be used.

When the HIPE foam is to be used as an absorbent for blood-based liquids, it is washed to lower the level of residual electrolytes less than about 2%. The removal of most of the residual electrolyte (i.e., hydratable salts) from the foam is particularly important. As noted previously, these hydratable salts are typically included during initial formation of the HIPE to minimize the tendency of monomers, comonomers, and crosslinkers that are primarily oil soluble to also dissolve in the water phase. However, after polymerization of the HIPE, the presence of these salts is unnecessary and can adversely affect the ability of the foam to absorb blood and blood-based liquids such as menses, especially as the concentration of these salts in the foam increases. Accordingly, it desirable to reduce the level of these hydratable salts in the foam during this washing step. After washing, the foams of the present invention have less than about 2% of such residual hydratable salts. Preferably, the foams of the present invention have less than about 1.0% of such residual salts, more preferably between about 0.15% and about 0.5%, and most preferably between about 0.25% and about 0.35% as calcium chloride by weight of the dry foam.

The washed foam is then treated with an effective amount of a suitable hydrophilizing surfactant. The treatment of the washed foam with a hydrophilizing surfactant is generally needed to render the foam relatively more hydrophilic, particularly for those HIPE foams intended for use as absorbents for blood and blood-based liquids such as menses. The hydrophilizing surfactant(s) used in the process of making the foam can be any material that enhances the water wettability of the HIPE foam surface. Suitable surfactants should be non-toxic and non-irritating to mucus membranes. The surfactants should be soluble or dispersible in warm water. Preferably, the hydrophilizing surfactant is a liquid at temperatures near ambient for ease of incorporation into a water solution. A particularly preferred surfactant is PEGOSPERSE 200 ML sold by Stepan Chemical Corp., Northfield, Ill., an ethoxylate of lauric acid having an average of 4.5 ethoxy units. The surfactant is preferably combined with about 0.05% aqueous $CaCl_2$.

The hydrophilizing surfactant can be dissolved or dispersed in a hydrophilizing solution that is applied to the HIPE foam surface. In this manner, hydrophilizing surfactants can be adsorbed by the preferred HIPE foams in amounts suitable for rendering the surfaces thereof substantially hydrophilic, but without substantially impairing the desired flexibility and compression deflection characteristics of the foam. Treatment of the HIPE foam with the hydrophilizing surfactant continues until the foam exhibits the desired degree of wettability. In preferred foams, the hydrophilizing surfactant is incorporated such that residual amounts of the surfactant that remain in the foam structure are typically in the range from about 0.1% to about 5%, preferably from about 0.2% to about 1%, by weight of the foam.

The washed foam is then dewatered to a moisture content of about 40% or less. Dewatering can be achieved by compressing the foam (preferably in the z-direction) to squeeze out residual water, by subjecting the foam and the water therein to temperatures of from about 60° to about 200° C., or to microwave treatment, by vacuum dewatering or by a combination of compression and thermal drying/microwave/vacuum dewatering techniques. The dewatering step will generally be carried out until the HIPE foam is ready for use and is as dry as practicable. Frequently such compression dewatered foams will have a water (moisture) content of from about 50 to about 500%, more preferably from about 50 to about 200%, by weight on a dry weight basis. Subsequently, the compressed foams can be thermally dried to a moisture content of about 40% or less, preferably in the range of from about 5 to about 15%, on a dry weight basis.

Alternative Foam Embodiments

In other embodiments, the characteristics of the foam used in the absorbent core can be varied. For example, the foams used in the present invention typically have a homogeneous structure, i.e., each portion of the absorbent core 24 is relatively uniform in terms of cell and hole sizes. However, if desired, these foams can be prepared so as to have a heterogeneous structure. For example, the foams can have regions of lower and higher capillary specific surface area and/or decreasing average cell size from their top (or portion closest to the wearer) to their bottom to provide a capillary gradient. The foams can have two ("bi-modal") or more cell sizes. The capillary gradient can be continuous or stepped between the different regions of the absorbent core. Such gradients can be achieved by varying the process conditions used in making the foam. Alternatively, the different foams could be formed side-by-side, and the portion of the foam with a lower capillarity can be folded over a portion of the foam with higher capillarity. Numerous other folded and pleated embodiments are possible the portions of the foam can be folded over each other to create a vertically stacked arrangement, an arrangement where the folded or pleated layers are side-by-side, or more complicated arrangements where the folded portions are at an angle with the other portions of the foam.

In another example, the foam can have regions of high and low capillary specific surface area, such as along the length versus the width of the foam. This provides the ability to control the direction of movement of the absorbed fluid within the foam and is particularly advantageous when the foam has a rectangular configuration. By providing a heterogeneous structure, the absorbed liquids can be induced to move along the length of the foam, as opposed to its width, thereby minimizing potential leakage along the sides of the catamenial product that can occur more readily if the foam has a homogeneous structure. The regions of high and low capillary specific surface area described above can be obtained by using multiple mixing heads, such as is described in the aforementioned U.S. Pat. No. 5,856,366, or by "pulsed" conditions during the making or delivering the HIPE, such as changes in mixer speed and/or by adjusting the water to oil phase ratio.

EXAMPLE 1

HIPE Preparation

This example illustrates the preparation of a molded tridimensional HIPE foam suitable for use as an absorbent core in a catamenial product. An aqueous phase is prepared containing the ingredients shown in Table 1. The oil phase is prepared using the ingredients shown in Table 2.

TABLE 1

Aqueous Phase Composition for HIPE.

| Component | Foam A |
| --- | --- |
| Water | QS |
| Potassium Persulfate | 0.05% |
| Calcium Chloride | 10.0% |

TABLE 2

"Oil Phase" Composition for HIPE.

| Component | Foam A |
| --- | --- |
| 2-ethylhexyl acrylate | 59.4% |
| styrene | 30% |
| divinyl benzene* | 15.6% |
| diglycerol monooleate | 8%** |

*Divinyl benzene in this table is a special blend comprising 45% ethyl styrene and 55% divinyl benzene, unless otherwise specified.
**Addition level of emulsifier and other adjuvants to the oil phase are "add-on" percentages; monomer composition sums to 100%. The 8% of emulsifier is actually 8 parts per 108 parts.

Controlled ratios of the oil phase stream (25° C.) and water phase are fed to a dynamic mixing apparatus, described in more detail in U.S. Pat. No. 5,387,207 (Dyer et al.) issued Feb. 7, 1995. Appropriate mixing of the combined streams in the dynamic mixing apparatus is achieved by means of pin impellers in mixing cylinders. The HIPE is produced at a rate of 5.1 lb./min.

Molds similar to the one shown in FIG. 4 are then filled with the as described above HIPE. The polymer is cured therein at a temperature of 65° C. for about 18 hours to form molded HIPE implement (Foam A). The molded HIPE foam is then stripped from the molds.

The stripped, molded foam articles are then dewatered and rehydrophilized according to the following method:

1) Place 2 or 3 of the molded implements onto the apertured surface of a Buchner funnel (~28 cm diameter) that is attached to a 2 liter filtering flask. Place a latex rubber sheet over the top of the Buchner funnel and attach the filtering flask to a vacuum source. Maintain suction until the flow of liquid from the samples is substantially stopped.
2) Remove the samples and place them in hot tap water for 1 minute. Place them back on the Buchner funnel and again cover them with the latex rubber sheet. Attach the filtering flask to a vacuum source and maintain suction until the flow of liquid from the samples is substantially stopped.
3) Repeat Step 2 to provide two washings.
4) Soak the samples in an aqueous solution of 0.5% Pegosperse 200ML and 0.05% calcium chloride for 1 minute and dewater the samples as described in Step 2.
5) Allow the samples to air dry.
6) Repeat Steps 1 to 5 until all the samples have been dewatered and rehydrophilized.

Table 3: summarizes the conditions under which each HIPE stream was made along with relevant properties of the foams produced from these HIPE streams following curing.

TABLE 3

Preparative Conditions and Properties of Foam A.

| Property | Foam A |
|---|---|
| Water:Oil Ratio | 30 |
| Mixer RPM | 300 |
| Pour Temperature | 66° C. |
| Tg | 26° C. |
| RTCD | 77% |
| Free Absorbent Capacity | 30 g/g |
| Density* | 0.033 g/cc |
| Portion in Product | Core 24 |

*Density in this and all following examples is measured on foams washed in water and 2-propanol to remove residual salts and wetting agents.

EXAMPLE 2

This example shows the preparation of HIPE foams with properties more tailored to use in specific portions of a core for an absorbent article. In particular, Foam B has properties suitable for use as an acquisition portion in the core of an absorbent article and Foam C has properties suitable for use as a storage portion in the core of an absorbent article. The composition of the HIPEs used to prepare these foams is shown in Tables 4 and 5. Table 6 shows the process conditions and the properties of the resulting foams.

TABLE 4

Aqueous Phase Composition for HIPE.

| Component | Foam B | Foam C |
|---|---|---|
| Water | QS | QS |
| Potassium Persulfate | 0.05% | 0.05% |
| Calcium Chloride | 10.0% | 10.0% |

TABLE 5

"Oil Phase" Composition for HIPE.

| Component | Foam B | Foam C |
|---|---|---|
| 2-ethylhexyl acrylate | 51.1% | 59.4% |
| styrene | 28% | 30% |
| divinyl benzene* | 20.9% | 15.6% |
| diglycerol monooleate | 5%** | 8%** |

*Divinyl benzene in this table is a special blend comprising 45% ethyl styrene and 55% divinyl benzene, unless otherwise specified.
**Addition level of emulsifier and other adjuvants to the oil phase are "add-on" percentages; monomer composition sums to 100%. The 8% of emulsifier is actually 8 parts per 108 parts.

TABLE 6

Preparative Conditions and Properties of Foam A.

| Property | Foam B | Foam C |
|---|---|---|
| Water:Oil Ratio | 30 | 26 |
| Mixer RPM | 300 | 675 |
| Pour Temperature | 66° C. | 66° C. |
| Tg | 26° C. | 46° C. |
| RTCD | 89% | 23% |
| Free Absorbent Capacity | 45 g/g | 26 g/g |
| Density* | 0.022 g/cc | 0.038 g/cc |
| Portion in Product | Acquisition | Storage |

The disclosures of all patents, patent applications (and any patents which issue thereon, as well as any corresponding published foreign patent applications), and publications mentioned throughout this description are hereby incorporated by reference herein. It is expressly not admitted, however, that any of the documents incorporated by reference herein teach or disclose the present invention.

While particular embodiments of the present invention have been illustrated and described, it would be obvious to those skilled in the art that various other changes and modifications can be made without departing from the spirit and scope of the invention.

What is claimed is:

1. A method of producing a molded, foam implement having a three dimensional shape, the method comprising the steps of:
    a) providing a water phase, said water phase comprising a polymerization initiator;
    b) providing an oil phase, said oil phase comprising:
        (i) from about 80% to about 98% by weight of a monomer component capable of forming a copolymer having a Tg value of from about −40° C. to about 90° C., said monomer component comprising:
            1) from about 10% to about 80% by weight of a substantially water-insoluble, monofunctional monomer capable of forming a homopolymer having a Tg of about 35° C. or less;
            2) from about 10% to about 70% by weight of a substantially water-insoluble, monofunctional comonomer capable of imparting toughness about equivalent to that provided by styrene;
            3) from about 2% to about 50% of a substantially water-insoluble, polyfunctional crosslinking agent selected from the group consisting of divinyl benzene, analogs of divinyl benzene, diacrylates of diols, analogs of diacrylates of diols, and mixtures thereof; and (ii) from about 2% to about 20% by weight of an emulsifier component which is soluble in said oil phase and which is suitable for forming a stable water-in-oil emulsion;

wherein said oil phase is substantially immiscible with said water phase and the ratio of said water phase to said oil phase (water:oil ratio) is between about 15:1 and about 125:1;

c) delivering both of said phases to a mixing means, wherein said water phase is delivered at a first flow rate and said oil phase is delivered at a second flow rate, wherein said flow rates are in a relationship defined by said water:oil ratio;

d) processing said water and oil phases using said mixing means, wherein said mixing means provides sufficient shear so as to emulsify said water phase in said oil phase so as to provide a continuous flow of a high internal phase emulsion (HIPE) having an internal phase size distribution;

e) providing a sequence of mold cavities, each of said mold cavities having a predetermined three dimensional configuration defined by a cavity wall wherein said three dimensional configuration is defined by said shape of said implement;

f) depositing said HIPE in one of said sequence of mold cavities using a HIPE delivery means;

g) curing said HIPE in said mold cavity so as to produce a molded HIPE foam having a cell size distribution that substantially conforms to said internal phase size distribution;

h) removing said molded HIPE foam from said mold; and i) repeating steps f through h until one of said oil phase and said water phase becomes depleted such that step c can no longer be accomplished, wherein said steps are repeated at a rate that is high enough that said HIPE is deposited into said mold cavity before said HIPE reaches a gel point.

2. A method according to claim 1 wherein steps e through i are accomplished by an injection molding process.

3. A method according to claim 1 wherein step f is accomplished by providing a pair of converging belts each of said belts having a plurality of mold cavity halves thereon wherein said mold cavity halves mate as said belts converge to form said mold cavity.

4. A method according to claim 1 wherein:

the HIPE provided by step c comprises a first HIPE having a first internal phase size distribution;

the mold cavities of step e comprise an assembly of first mold cavity segments that are mated to form first mold cavities;

step f comprises depositing said first HIPE into one of said first mold cavities;

step g comprises curing said first HIPE in said first mold cavity to form a pre-molded HIPE foam;

and steps h and i are replaced by the following steps:

h) processing a second water phase and a second oil phase, provided according to steps a, b and c, using a second mixing means according to steps a, b and c, wherein said second mixing means provides sufficient shear so as to emulsify said second water phase in said second oil phase so as to provide a continuous flow of a second high internal phase emulsion (HIPE) having a second internal phase size distribution that differs from said first internal phase size distribution, said water and oil phases being provided according to steps a through c;

i) removing one or more of said mold first cavity segments from said first mold cavity to expose said pre-molded HIPE foam, said pre-molded HIPE foam being carried by a remaining portion of said mold cavity segments;

j) providing a sequence of one or more second mold cavity segments and mating said segments with said residual portion of said first mold cavity segments to form a sequence of second mold cavities;

k) depositing said second HIPE in one of said sequence of second mold cavities using a second HIPE delivery means;

l) curing said second HIPE in said second mold cavity so as to produce a second molded HIPE foam having a second cell size distribution that substantially conforms to said second internal phase size distribution so as to form a molded foam implement;

m) removing said molded foam implement from said mold; and n) repeating steps e through m until one of said oil phase and said water phase becomes depleted such that step k can no longer be accomplished, wherein said steps are repeated at a rate that is high enough such that both of said HIPEs are deposited into said mold cavities before either of said HIPE reaches a gel point.

5. A method according to claim 1 wherein said three-dimensional, molded, foam implement comprises a component of an absorbent article.

6. A method according to claim 5 wherein said component comprises an absorbent component.

7. A method according to claim 5 wherein said component has a predetermined shape designed to substantially conform to at least a portion of a wearer's body.

8. A method according to claim 1 wherein said three-dimensional, molded, foam implement comprises a toy.

9. A method according to claim 1 wherein said three-dimensional, molded, foam implement comprises a filter element.

10. A method according to claim 1 wherein said three-dimensional, molded, foam implement comprises an insulating material.

11. A method according to claim 1 wherein said monomer component is capable of forming a copolymer having a Tg value of from about −40° C. to about 30° C.

12. A method according to claim 11 wherein said monomer component is capable of forming a copolymer having a Tg value of from about −20° C. to about 30° C.

13. A method according to claim 1 wherein said monomer component comprises from about 40% to about 80% by weight of a substantially water-insoluble, monofunctional monomer capable of forming a homopolymer having a Tg of about 35° C. or less.

14. A method, according to claim 13 wherein said monomer component comprises from about 50% to about 70% by weight of a substantially water-insoluble, monofunctional monomer capable of forming a homopolymer having a Tg of about 35° C. or less.

15. A method according to claim 1 wherein said monomer component comprises from about 20% to about 50% by weight of a substantially water-insoluble, monofunctional comonomer capable of imparting toughness about equivalent to that provided by styrene.

16. A method according to claim 15 wherein said substantially water-insoluble, monofunctional comonomer capable of imparting toughness about equivalent to that provided by styrene is selected from the group consisting of styrene, methyl methacrylate, isoprene, piperylene, dimethylbutadiene, and mixtures thereof.

17. A method according to claim 1 wherein each of said cavities in said sequence is connected to cavities lying adjacent thereto by an isthmus.

18. A method according to claim 4 wherein each of said cavities in said sequence is connected to cavities lying adjacent thereto by an isthmus.

19. A method according to claim 1 wherein a substantially liquid impermeable membrane is interposed between said HIPE and at least a portion of said cavity wall so that said HIPE is cured while in contact with said membrane.

* * * * *

UNITED STATES PATENT AND TRADEMARK OFFICE
CERTIFICATE OF CORRECTION

PATENT NO. : 6,406,648 B1
DATED : June 18, 2002
INVENTOR(S) : Noel et al.

It is certified that error appears in the above-identified patent and that said Letters Patent is hereby corrected as shown below:

Column 19,
Line 59, please delete "H1PEs" and insert therefor -- HIPEs --.

Column 20,
Line 63, please delete "vinyl4,6-" and insert therefor -- vinyl 4,6- --.

Column 23,
Line 10, please delete "C $\cdot_6$" and insert therefor -- $C_{16}$ --.

Column 29,
Line 8, please delete "maybe" and insert therefor -- may be --.
Line 17, please delete "RIPE" and insert therefor -- HIPE --.

Column 30,
Line 8, please delete "50°0 C." and insert therefor -- 50° C. --.

Column 33,
Line 27, after "Table 3" please delete ":" (the colon).

Column 36,
Line 52, after "method", please delete "," (the comma).

Signed and Sealed this

Twenty-ninth Day of June, 2004

JON W. DUDAS
*Acting Director of the United States Patent and Trademark Office*